United States Patent [19]
Hromas

[11] Patent Number: 6,096,300
[45] Date of Patent: Aug. 1, 2000

[54] TREATMENT OF MYELOPROLIFERATIVE DISEASE WITH EXODUS CHEMOKINE

[75] Inventor: Robert Hromas, Indianapolis, Ind.

[73] Assignee: Advanced Research and Technology Institute, Bloomington, Ind.

[21] Appl. No.: 08/970,403

[22] Filed: Nov. 14, 1997

Related U.S. Application Data

[63] Continuation-in-part of application No. 08/749,513, Nov. 15, 1996, abandoned.

[51] Int. Cl.$^7$ .................................................... A61K 38/19
[52] U.S. Cl. ................................. 424/85.1; 514/2; 514/8
[58] Field of Search ............................... 424/85.1; 514/2, 514/8

[56] References Cited

U.S. PATENT DOCUMENTS

| | | | |
|---|---|---|---|
| 4,965,392 | 10/1990 | Fritzberg et al. | 558/254 |
| 5,037,630 | 8/1991 | Fritzberg et al. | 424/1.1 |
| 5,179,078 | 1/1993 | Rollins et al. | 514/2 |
| 5,413,778 | 5/1995 | Kunkel et al. | 424/1.41 |
| 5,602,008 | 2/1997 | Wilde et al. | 530/351 |

FOREIGN PATENT DOCUMENTS

| | | |
|---|---|---|
| WO 96/05856 | 2/1996 | WIPO . |
| WO 96/16979 | 6/1996 | WIPO . |
| WO 98/01557 | 1/1998 | WIPO . |

OTHER PUBLICATIONS

Ahuja, S.K. et al., "Chemokine receptors and molecular mimicry," *Immunology Today*, 15(6):281–287 (1994).

Alkhatib, G. et al., "CC CKR5: A RANTES, MIP–1α, MIP–1β Receptor as a Fusion Cofactor for Macrophage–Tropic HIV–1," *Science*, 272:1955–1958 (Jun. 28, 1996).

Avanzi, G.C. et al., "Selective growth response to IL–3 of a human leukaemic cell line with megakaryoblastic features," *British Journal of Haematology*, 69:359–366 (1988).

Baggiolini, M. et al., "Interleukin–8 and Related Chemotactic Cytokines–CXC and CC Chemokines," *Advances in Immunology*, 55:97–179 (1994).

Better, M. et al., "*Escherichia coli* Secretion of an Active Chimeric Antibody Fragment," *Science*, 240:1041–1043 (May 20, 1988).

Bitter, G.A. et. al., "Secretion of foreign proteins from *Saccharomyces cerevisiae* directed by α–factor gene fusions," *Proc. Natl. Acad. Sci., USA*, 81:5330–5334 (Sep., 1984).

Brown, K.D. et al., "A Family of Small Inducible Proteins Secreted by Leukocytes are Members of a New Superfamily that Includes Leukocyte and Fibroblast–Derived Inflammatory Agents Growth Factors, and Indicators of Various Activation Processes," *J. Immunology*, 42(2):679–687 (Jan. 15, 1989).

Broxmeyer, H.E. et al., "Enhancing and Suppressing Effects of Recombinant Murine Macrophage Inflammatory Proteins on Colony Formation In Vitro by Bone Marrow Myeloid Progenitor Cells," *Blood*, 76(6):1110–1116 (Sep. 15, 1990).

Broxmeyer, H.E. et al., "Comparative Analysis of the Human Macrophage Inflammatory Protein Family of Cytokines (Chemokines) on Proliferation of Human Myeloid Progenitor Cells," *J. Immunology*, 150(8):3448–3458 (Apr. 15, 1993).

(List continued on next page.)

*Primary Examiner*—Garnette D. Draper
*Attorney, Agent, or Firm*—Marshall, O'Toole, Gerstein, Murray & Borun

[57] ABSTRACT

The present invention provides purified and isolated chemokine protein, fragments and polypeptide analogs thereof, antibodies thereto, and materials and methods for the recombinant production thereof. These products are useful in therapeutics, such as the treatment of myeloproliferative diseases, as well as in diagnostic and medical imaging applications.

2 Claims, 8 Drawing Sheets

Days in Culture

□ Control
○ Exodus
■ GM-CSF + SCF
● Exodus + GM-CSF + SCF

OTHER PUBLICATIONS

Broxmeyer, H.E. et al., "Human chemokines: enhancement of specific activity and effects in Vitro on normal and leukemic progenitors and a factor–dependent cell line and in Vivo in mice," *Ann. Hematol.*, 71:235–246 (1995).

Chang, H.C. et al., "Cloning and expression of a γ–interferon–inducible gene in monocytes: a new member of a cytokine gene family," *International Immunology*, 1(4):388–397 (1989).

Chang, J–Y, "Thrombin specificity: Requirement for apolar amino acids adjacent to the thrombin cleavage site of polypeptide substrate," *Eur. J. Biochem.*, 151:217–224 (1985).

Charo, I.F. et al., "Molecular cloning and functional expression of two monocyte chemoattractant protein 1 receptors reveals alternative splicing of the carboxyl–terminal tails," *Proc. Nat. Acad. Sci.*, 91:2752–2756 (Mar., 1994).

Choe, H. et al., "The β–Chemokine Receptors CCR3 and CCR5 Facilitate Infection by Primary HIV–1 Isolates," *Cell*, 85:1135–1148 (Jun. 28, 1996).

Clark–Lewis, I. et al., "Structure–Activity Relationships of Interleukin–8 Determined Using Chemically Synthesized Analogs," *J. Biological Chemistry.*, 266(34):23128–23134 (Dec. 5, 1991).

Clark–Lewis, I. et al., "Structure–Activity Relationships of Chemokines," *J. Leukoc. Biol.*, 57:703–711 (May, 1995).

Cocchi, F. et al., "Identification of RANTES, MIP–1α, and MIP–1β as the Major HIV–Suppressive Factors Produced by CD8$^+$ T Cells," *Science*, 270:1811–1815 (Dec. 15, 1995).

Combadiere, C. et al., "Cloning and Functional Expression of a Human Eosinophil CC Chemokine Receptor," *J. Biological Chemistry*, 270(27):16491–16494 (Jul. 14, 1995).

Deng, H. et al., "Identification of a major co–receptor for primary isolates of HIV–1," *Nature*, 381:661–666 (Jun. 20, 1996).

Devi, S. et al., "Biologic Activities of the β–Chemokine TCA3 on Neutrophils and Macrophages," *J. Immunology.*, 154:5376–5383 (1995).

Doranz, B.J. et al., "A Dual–Tropic Primary HIV–1 Isolate That Uses Fusin and the β–Chemokine Receptors CKR–5, CKR–3, and CKR–2b as Fusion Cofactors," *Cell*, 85:1149–1158 (Jun. 28, 1996).

Dragic, T. et al., "HIV–1 entry into CD4$^+$ cells is mediated by the chemokine receptor CC–CKR–5," *Nature*, 381:667–673 (Jun. 20, 1996).

Dunlop D.J. et al., "Demonstration of Stem Cell Inhibition and Myeloprotective Effects of SCI/rhMIP1α In vivo," *Blood*, 79(9):2221–2225 (May 1, 1992).

Ellis, L. et al., "Replacement of Insulin Receptor Tyrosine Residues 1162 and 1163 Compromises Insulin–Stimulated Kinase Activity and Uptake of 2–Deoxyglucose," *Cell*, 45:721–732 (Jun. 6, 1986).

Fauci, A.S., "An elusive soluble suppressor," *Nature*, 378:561 (Dec. 7, 1995).

Feng, Y. et al., "HIV–1 Entry Cofactor: Functional cDNA Cloning of a Seven–Transmembrane, G Protein–Coupled Receptor," *Science*, 272:872–877 (May 10, 1996).

Harada, A. et al., "Essential involvement of interleukin–8 (IL–8) in acute inflammation," *J. Leukocyte Biology*, 56:559–564 (Nov., 1994).

Ho, D.D., "Viral Counts Count in HIV Infection," *Science*, 272:1124–1125 (May 24, 1996).

Holmes, W.E. et al., "Structure and Functional Expression of a Human Interleukin–8 Receptor," *Science*, 253:1278–1280 (Sep. 13, 1991).

Horuk, R. et al., "Purification, Receptor Binding Analysis, and Biological Characterization of Human Melanoma Growth Stimulating Activity (MGSA)," *J. Biological Chemistry*, 268(1):541–546 (Jan. 5, 1993).

Horuk, R., "Molecular Properties of the Chemokine Receptor Family," *TIPS*, 15:159–165 (May, 1994).

Hromas, R. et al., "Exodus, A Novel Chemokine that Inhibits Proliferation of Hematopoietic Progenitors and Production of HIV," *Blood*, 88(10 Suppl. 1 part 1–2): 339A (1996). Abstract 1344.

Hromas, R. et al., "Isolation and Characterization of Exodus–2, a Novel C–C Chemokine with a Unique 37–Amino Acid Carboxyl–Terminal Extension," *J. Immunology*, 159:2554–2558 (1997).

Hromas, R. et al., "Cloning and characterization of exodus, a novel β–chemokine." *Blood*, 89(9):3315–3322 (May, 1997).

Keller, H.U. et al., "Re–Assessment of Boyden's Technique for Measuring Chemotaxis," *J. Immunological Methods*, 1:165–168 (1972).

Kuna, P. et al., "RANTES, a Monocyte and T Lymphocyte Chemotactic Cytokine Releases Histamine from Human Basophils," *J. Immunology*, 49(2):636–642 (Jul. 15, 1992).

Kurjan J. et al., "Structure of a Yeast Pheromone Gene (MFα): A Putative α–Factor Precursor Contains Four Tandem Copies of Mature α–Factor," *Cell*, 30:933–943 (Oct., 1982).

Laning, J. et al., "Inhibition of In Vivo Tumor Growth by the β Chemokine, TCA3," *J. Immunology*, 153:4625–4635 (1994).

Lord, B.I. et al., "Macrophage–Inflammatory Protein Protect Multipotent Hematopoietic Cells From the Cytotoxic Effects of Hydroxyurea In Vivo," *Blood*, 79(10):2605–2609 (May 15, 1992).

Luo, Y. et al., "Biologic Activities of the Murine β–Chemokine TCA3," *J. Immunology*, 153:4616–4624 (1994).

Mantel, C. et al., "Polymerization of murine macrophage inflammatory protein 1α inactivates its myelosuppressive effects in vitro: The active form is a monomer," *Proc. Natl. Acad. Sci., USA*, 90:2232–2236 (Mar., 1993).

Martinet, Y. et al., "Blood monocyte chemotaxis," *J. Immunological Methods*, 174:209–214 (1994).

Matsushima, K. et al., "Purification and Characterization of a Novel Monocyte Chemotactic and Activating Factor Produced by a Human Myelomonocytic Cell Line," *J. Experimental Medicine*, 169:1485–1490 (1989).

Meurer, R. et al., "Formation of Eosinophilic and Monocytic Intradermal Inflammatory Sites in the Dog by Injection of Human RANTES but not Human Monocyte Chemoattractant Protein 1, Human Macrophage Inflammatory Protein 1α, or Human Interleukin 8," *J. Exp. Med.*, 178:1913–1921 (Dec., 1993).

Miller, M.D. et al., "A Novel Polypeptide Secreted by Activated Human T Lymphocytes," *J. Immunology*, 3(9):2907–2916 (Nov. 1, 1989).

Murphy, P.M. et al., "Cloning of Complementary DNA Encoding a Functional Human Interleukin–8 Receptor," *Science*, 253:1280–1283 (Sep. 13, 1991).

Murphy, P.M., "The Molecular Biology of Leukocyte Chemoattractant Receptors," *Ann. Rev. Immnol.*, 12:593–633 (1994).

Nakao, M. et al., "Structures of Human Genes Coding for Cytokine LD78 and Their Expression," *Molecular Cellular Biology*, 10(7):3646–3658 (Jul., 1990).

Neote, K. et al., "Molecular Cloning. Functional Expression. and Signaling Characteristics of a C–C Chemokine Receptor," *Cell*, 72:415–425 (Feb. 12, 1993).

Oppenheim, J.J., "Overview of Chemokine ," in *The Chemokines*, I.J.D. Lindley et al., eds., Plenum Press, NY, pp. 183–186 (1993).

Paxton, W.A. et al., "Relative resistance to HIV–1 infection of CD4 lymphocytes from persons who remain uninfected despite multiple high–risk sexual exposures," *Nature Medicine*, 2(4):412–417 (Apr., 1996).

Power, C.A. et al., "Molecular Cloning and Functional Expression of a Novel CC Chemokine Receptor cDNA from a Human Basophilic Cell Line," *J. Biological . Chemistry*, 270(33):19495–19500 (Aug. 18, 1995).

Price et al., "Expression, purification and characterization of recombinant murine granulocyte–macrophage colony–stimulating factor and bovine interleukin–2 from yeast," *Gene*, 55:287–293 (1987).

Raport, C.J. et al., "Molecular Cloning and Functional Characterization of a Novel Human CC Chemokine Receptor (CCR5) for RANTES, MIP–1β, and MIP–1α," *J. Biological Chemistry*, 271(29):17161–17166 (Jul. 19, 1996).

Rose, A.B. et al., "Propagation and Expression of Cloned Genes in Yeast: 2–μm Circle–Based Vectors," *Methods in Enzymology*, 185:234–279 (1990).

Rosenthal, N., "Identification of Regulatory Elements of Cloned Genes with Functional Assays," *Methods in Enzymology*, 152:704–720 (1987).

Rothenberg, M.E. et al., "Constitutive and Allergen–induced Expression of Eotaxin mRNA in the Guinea Pig Lung," *J. Exp. Med.*, 181:1211–1216 (Mar., 1995).

Sambrook et al., *Molecular Cloning: a Laboratory Manual*, Chapter 15, Second Edition, Cold Spring Harbor, New York: Cold Spring Harbor Laboratory (1989).

Sarris, A.H. et al., "Human Interferon–inducible Protein 10: Expression and Purification of Recombinant Protein Demonstrate Inhibition of Early Human Hematopoietic Progenitors," *J. Exp. Med.*, 178:1127–1132 (Sep., 1993).

Schall, T.J. et al., "A Human T Cell–Specific Molecule is a Member of a New Gene Family," *J. Immunology*, 141(3):1018–1025 (Aug. 1, 1988).

Springer, T.A., "Traffic Signals for Lymphocyte Recirculation and Leukocyte Emigration: The Multistep Paradigm," *Cell*, 76:301–314 (Jan. 28, 1994).

Stearns, T. et al., "Manipulating Yeast Genome Using Plasmid Vectors," *Meth. Enz.*, 185:280–297 (1990).

Takeda, J. et al., "A molecular inventory of human pancreatic islets: sequence analysis of 1000 cDNA clones," *Human Molecular Genetics*, 2(11):1793–1798 (1993).

Urlab, G. et al., "Deletion of the Diploid Dihydrofolate Reductase Locus from Cultured Mammalian Cells," *Cell*, 33:405–412 (Jun., 1983).

Van Damme, J. et al., "Structural and Functional Identification of Two Human, Tumor–derived Monocyte Chemotactic Proteins (MCP–2 and MCP–3) Belonging to the Chemokine Family," *J. Exp. Med.*, 176:59–65 (Jul., 1992).

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 821 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 43..327

(ix) FEATURE:
        (A) NAME/KEY: mat_peptide
        (B) LOCATION: 109..327

(xi) SEQUENCE DESCRIPTION: SEQ ID NO:1:

GGTACTCAAC ACTGAGCAGA TCTGTTCTTT GAGCTAAAAA CC ATG TGC TGT ACC           54
                                                Met Cys Cys Thr
                                                -22       -20

AAG AGT TTG CTC CTG GCT GCT TTG ATG TCA GTG CTG CTA CTC CAC CTC        102
Lys Ser Leu Leu Leu Ala Ala Leu Met Ser Val Leu Leu Leu His Leu
            -15                 -10                  -5

TGC GGC GAA TCA GAA GCA AGC AAC TTT GAC TGC TGT CTT GGA TAC ACA        150
Cys Gly Glu Ser Glu Ala Ser Asn Phe Asp Cys Cys Leu Gly Tyr Thr
    1               5                   10
```

```
GAC CGT ATT CTT CAT CCT AAA TTT ATT GTG GGC TTC ACA CGG CAG CTG      198
Asp Arg Ile Leu His Pro Lys Phe Ile Val Gly Phe Thr Arg Gln Leu
 15                  20                  25                  30

GCC AAT GAA GGC TGT GAC ATC AAT GCT ATC ATC TTT CAC ACA AAG AAA      246
Ala Asn Glu Gly Cys Asp Ile Asn Ala Ile Ile Phe His Thr Lys Lys
                 35                  40                  45

AAG TTG TCT GTG TGC GCA AAT CCA AAA CAG ACT TGG GTG AAA TAT ATT      294
Lys Leu Ser Val Cys Ala Asn Pro Lys Gln Thr Trp Val Lys Tyr Ile
                 50                  55                  60

GTG CGT CTC CTC AGT AAA AAA GTC AAG AAC ATG TAAAAACTGT GCCTTTTCTG    347
Val Arg Leu Leu Ser Lys Lys Val Lys Asn Met
                 65                  70

GAATGGAATT GGACATAGCC CAAGAACAGA AAGAACCTTG CTGGGGTTGG AGGTTTCACT    407

TGCACATCAT GGAGGGTTTA GTGCTTATCT AATTTGTGCC TCACCTGGAC TTGTCCAATT    467

AATGAAGTTG ATTCATATTG CATCATAGTT TGCTTTGTTT AAGCATCACA TTAAAGTTAA    527

ACTGTATTTT ATGTTATTTA TAGCTGTAGG TTTTCTGTGT TTAGCTATTT AATACTAATT    587

TTCCATAAGC TATTTTGGTT TAGTGCAAAG TATAAAATTA TATTTGGGGG GGAATAAGAT    647

TATATGGACT TTCTTGCAAG CAACAAGCTA TTTTTTAAAA AAAACTATTT AACATTCTTT    707

TGTTTATATT GTTTTGTACT CCTAAATTGT TGTAATTGCA TTATAAAATA AGAAAAATAT    767

TAATAAGACA AATATTGAAA ATAAAGAAAC AAAAAGTTCT TCTGTTAAAA AAAA          821

(2) INFORMATION FOR SEQ ID NO:2:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:2:

Met Cys Cys Thr Lys Ser Leu Leu Leu Ala Ala Leu Met Ser Val Leu
-22         -20                 -15                 -10

Leu Leu His Leu Cys Gly Glu Ser Glu Ala Ser Asn Phe Asp Cys Cys
        -5                   1                   5                  10

Leu Gly Tyr Thr Asp Arg Ile Leu His Pro Lys Phe Ile Val Gly Phe
                 15                  20                  25

Thr Arg Gln Leu Ala Asn Glu Gly Cys Asp Ile Asn Ala Ile Ile Phe
                 30                  35                  40

His Thr Lys Lys Lys Leu Ser Val Cys Ala Asn Pro Lys Gln Thr Trp
                 45                  50                  55

Val Lys Tyr Ile Val Arg Leu Leu Ser Lys Lys Val Lys Asn Met
                 60                  65                  70

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:3:

GGCGAAGCTT TGAGCTAAAA ACCATG                                         26
```

-continued (2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO:4:

GCGGGAATTC TTACATGTTC TTGACT                26

TREATMENT OF MYELOPROLIFERATIVE DISEASE WITH EXODUS CHEMOKINE

This application is a contintitation-in-part of U.S. Ser. No. 08/749,513 filed Nov. 15, 1996 now abandoned incorporated herein by reference.

The present invention relates generally to chemokines and more particularly to purified and isolated polynucleotides encoding a human C—C chemokine designated Exodus and analogs thereof, to purified and isolated chemokine polypeptides encoded by the polynucleotides, to materials and methods for the recombinant production of these polypeptides, and therapeutic uses of these polypeptides, particularly in myeloprotection during chemotherapy, in treatment of myeloproliferative diseases, and for acquired immunodeficiency syndrome (AIDS).

BACKGROUND OF THE INVENTION

Chemokines, also known as "intercrines" and "SIS cytokines", comprise a superfamily of small secreted proteins (approximately 70–100 amino acids and 8–12 kilodaltons in size) which primarily regulate leukocyte migration and activation, and thereby aid in the stimulation and regulation of the immune system. The name "chemokine" is derived from the term chemotactic cytokine, and refers to the ability of these proteins to stimulate chemotaxis of leukocytes. Indeed, chemokines may comprise the main attractants for inflammatory cells into pathological tissues. [See generally, Baggiolini et al., *Advances in Immunology*, 55:97–179 (1994); Oppenheim, The Chemokines, Lindley et al., eds., pages 183–186, Plenum Press, N.Y. (1993))]. While chemokines are generally secreted by leukocytes, several chemokines are expressed in a multitude of tissues. Baggiolini et al., supra, Table II. Some chemokines also activate or attract a variety of cell types in addition to leukocytes, such as endothelial cells and fibroblasts.

Previously identified chemokines generally exhibit 20–70% amino acid identity to each other and contain four highly-conserved cysteine residues. Based on the relative position of the first two of these cysteine residues, chemokines have been further classified into two subfamilies. In the "C-X-C" or "α" subfamily, encoded by genes localized to human chromosome 4, the first two cysteines are separated by one amino acid. In the "C—C" or "β" subfamily, encoded by genes which have been mapped to human chromosome 17, the first two cysteines are adjacent. X-ray crystallography and NMR studies of several chemokines have indicated that, in each family, the first and third cysteines from a first disulfide bridge, and the second and fourth cysteines form a second disulfide bridge, strongly influencing the native conformation of the proteins. In humans alone, nearly ten distinct sequences have been described for each chemokine subfamily. Chemokines of both subfamilies have characteristic leader sequences of twenty to twenty-five amino acids.

The C-X-C chemokines, which include IL-8, GROα/β/γ, platelet basic protein, Platelet Factor 4 (PF4), neutrophil-activating peptide-2 (NAP-2), macrophage cheinotactic and activating factor (MCAF), IP-10, and others, share approximately 25% to 60% identity when any two amino acid sequences are compared (except for the GROα/β/γ members, which are 84–88% identical with each other). Most of the subfamily members (excluding IP-10 and Platelet Factor 4) share a common E-L-R tri-peptide motif upstream of the first two cysteine residues. The C-X-C chemokines are generally potent stimulants of neutrophils, causing rapid shape change, chemotaxis, respiratory bursts, and degranulation. Specific truncation of the N-terminal amino acid sequence of certain C-X-C chemokines, including IL-8, is associated with marked increases in activity.

The C—C chemokines, which include Macrophage Inflammatory Proteins MIP-1α [Nakao et al., *Mol. Cell Biol.*, 10:3646 (1990)] and MIP-1β [Brown et al., *J. Immunol.*, 142:679 (1989)], Monocyte Chemotactic Proteins MCP-1 [Matsushima et al., *J. Exp. Med.*, 169:1485 (1989)], MCP-2 [Van Damme et al., *J. Exp. Med.*, 176:59 (1992) and Chang et al., *Int. Immunol.*, 1:388 (1989)], and MCP-3 [Van Damme et al., supra], RANTES [Schall et al., *J. Immunol.*, 141:1018 (1988)], I-309 [Miller et al., *J. Immunol.*, 143:2907 (1989)], eotaxin [Rothenberg et al., *J. Exp. Med.*, 181:1211–1216 (1995)] and others, share 25% to 70% amino acid identity with each other. The C—C chemokines generally activate monocytes, lymphocytes, basophils and eosinophils, but not neutrophils. Most of the reported C—C chemokines activate monocytes, causing calcium flux and chemotaxis. More selective effects are seen on lymphocytes, for example, T-lymphocytes, which respond most strongly to RANTES.

C—C chemokines can be further subdivided according to structural homologies and similar activities. MIP-1α, MIP-1β and RANTES have closer homology and range of biological activities than the other members of the family. Another subfamily within the C—C chemokine family are the monocyte chemotactic proteins (MCP), which are structurally more similar to each other than to other members of the C—C chemokine family, and which preferentially stimulate monocytes to migrate and respond to inflammatory stimuli.

Studies with deletion and substitution analogs have revealed that the critical receptor binding regions appear to be primarily in the amino-terminal residues of the chemokines, followed by a second region in the loop following the second cysteine. These general requirements for function appear to be common to all chemokines. [Clark-Lewis et al., *J. Leukocyte Bio.*, 57:703 (1995).]

The chemokine receptors are seven-transmembrane-domain rhodopsin-like G protein-coupled receptors. A receptor specific for IL-8 has been cloned by Holmes et al., *Science*, 253:1278–83 (1991), while a similar receptor (77% identity) which recognizes IL-8, GRO and NAP-2 has been cloned by Murphy and Tiffany, *Science*, 253:1280–83 (1991). Five of the C—C chemokine receptors have been cloned to date: a C—C chemokine receptor-1 (CCR-1) which recognizes MIP-1α and RANTES [Neote et al., *Cell*, 72:415–425 (1993)], a receptor (CCR-4) for MIP-1α, RANTES and MCP-1 [Power et al., *J. Biol. Chem.*, 270:19495–19500 (1995)], an MCP-1 receptor (CCR-2B) [Charo et al., *Proc. Nat. Acad. Sci.*, 91:2752–56 (1994)], an eotaxin receptor (CCR-3) [Combadiere et al., *J. Biol. Chem.* 270:16491–16494 (1995)], and a receptor (CCR-5) for MIP-1α, MIP-1β and RANTES [Raport et al., *J. Biol. Chem.*, 271:17161–17166 (1996)].

These receptors tend to be multifunctional, and may bind a number of different chemokines. The receptors themselves may play a role in human disease. For example, the Duffy antigen on human red blood cells (also known as the erythrocyte chemokine receptor), which binds avidly to chemokines including IL-8, NAP-2, GROα, RANTES, MCP-1, is an invasion receptor for a malaria-causing parasite, *Plasmodium knowlesi*. Two herpesviridae, *Herpesvirus saimiri* and human cytomegalovirus, also appear to encode functional chemokine receptor homologs. [Ahuja et al., *Immunol. Today*, 15:281-(1994); Murphy, *Ann. Rev. Immunol.*, 12:593–633 (1994); Horuk, *TIPS*, 15:159 (1994).]

Because of their pro-inflammatory activities, chemokines are believed to play a role in a wide variety of diseases involving inflammatory tissue destruction, such as rheumatoid arthritis, myocardial infarction, and adult respiratory distress syndrome. The role of a number of chemokines, particularly the C-X-C chemokine IL-8, has been well documented in various pathological conditions. See generally Baggiolini et al., supra, Table VII. For example, several studies have observed high levels of IL-8 in the synovial fluid of inflamed joints of patients suffering from rheumatic diseases, osteoarthritis, and gout. Psoriasis has also been linked to over-production of IL-8.

The role of C—C chemokines in pathological conditions has also been documented. For example, the concentration of MCP-1 is higher in the synovial fluid of patients suffering from rheumatoid arthritis than that of patients suffering from other arthritic diseases. The MCP-1 dependent influx of mononuclear phagocytes may be an important event in the development of idiopathic pulmonary fibrosis. The role of C—C chemokines in the recruitment of monocytes into atherosclerotic areas is currently of intense interest, with enhanced MCP-1 expression having been detected in macrophage-rich arterial wall areas but not in normal arterial tissue. MCPs may also be involved in induction of angiogenesis and tumor growth or metastasis. Expression of MCP-1 in malignant cells has been shown to suppress the ability of such cells to form tumors in vivo. (See U.S. Pat. No. 5,179,078, incorporated herein by reference.)

Other chemokine activities include the ability to inhibit the proliferation of bone marrow progenitor cells. Recombinant MIP-1α, but not MIP-1β, has been shown to suppress myelopoiesis of stein and progenitor cells, and appears to be selective in its ability to suppress growth factor-stimulated proliferation of multipotential progenitor cells (colony forming units of granulocyte-erythroid-macrophage-megakaryocytes, CFU-GEMM) and subpopulations of burst-forming units of erythroid (BFU-E) and colony-forming units of granulocytes-macrophages (CFU-GM) progenitor cells. [Broxmeyer et al., *Blood*, 76:1110–1116 (1990).] These effects are not a cytotoxic effect, but rather a cell cycle arrest. MIP-2α, IL-8, PF4 and MCAF also have been reported to be suppressors of hemopoietic stem/progenitor cell proliferation. [Broxmeyer et al., *J. Immunol.*, 150:3448–3458 (1993); Broxmeyer et al., *Ann. Hematol.*, 71:235–246 (1995).] These chemokines appear to act directly at the level of the myeloid progenitors. Some reports indicate that MIP-1α has the potential to protect multipotent hematopoietic cells from the cytotoxic effects of chemotherapeutic agents. [Dunlop et al., *Blood*, 79:2221–2225 (1992) and Lord et al., *Blood*, 79:2605–2609 (1992).] Clinical trials are reportedly under way for the use of a MIP-1α, analog (designated BB10010, British Biotechnology) as a myeloprotective agent with Cytoxan® (cyclophosphamide from Bristol-Myers Squibb Oncology).

Recently, there have been several reports that some C—C chemokines, MIP-1α, MIP-1β and RANTES, inhibit human immunodeficiency virus (HIV) production. [Cocchi et al., *Science*, 270:1811 (1996); Fauci, *Nature*, 378:561 (1996).] One study has reported that CD4+ lymphocytes of individuals who have been exposed to HIV but remain HIV-negative express very high levels of these C—C chemokines. [Paxton et al., *Nature Med.*, 2:412 (1996).] A potential mechanism for this inhibition has been suggested by the isolation and identification of HIV co-receptors as members of the chemokine receptor families. The CCR-5 receptor which binds RANTES, MIP-1α and MIP-1β has been identified as the main co-receptor for most macrophage-tropic HIV strains [Deng et al., *Nature*, 381:661 (1996); Dragic et al., *Nature*, 381:667 (1996); Alkhatib et al., *Science*, 272:1955 (1996)]. It has been reported that occasional primary HIV-1 macrophage-tropic strains interact with the CCR-3 and CCR-2B receptors in vitro [Choe et al., *Cell*, 85:1135 (1996); Doranz et al., *Cell*, 85:1149 (1996)]. A chemokine receptor designated "Fusin" (now known as the C-X-C chemokine receptor CXCR-4) has been identified as a receptor for T-cell tropic strains of HIV [Feng et al., *Science*, 272:872 (1996)]. These HIV co-receptors are in the cheinokine receptor families, and appear to be cofactors with CD4 for the fusion and entry of HIV viruses into human target cells.

A need therefore exists for the identification and characterization of additional C—C chemokines, to further elucidate the role of this important family of molecules in pathological conditions and to develop improved treatments for such conditions utilizing chemokine-derived products.

Of interest to the present invention is International Publication No. WO 96/05856 published Feb. 29, 1996, which reports the identification of two chemokines termed human chemokine beta-4 (Ckβ-4) and human chemokine beta-10 (Ckβ-10) from cDNA libraries derived from human gall bladder and nine week human fetal tissue, respectively. Ckβ-4 is very similar in both DNA and amino acid sequence to the Exodus chemokine described herein (the differences being that Ckβ-4 has an additional alanine after residue 4 of the mature Exodus chemokine and that the reported deduced leader sequence of Ckβ-4 is 24 amino acids, compared to the 22 amino acid leader sequence of Exodus). No biological activities of either chemokine Ckβ-4 or Ckβ-10 were determined. In particular, the publication does not mention any potential role for these chemokines in the pathogenesis of HIV infection, nor does it specifically describe use of these chemokines for treating myeloproliferative diseases.

Also of interest is the cloning of another C—C chemokine, designated Exodus-2, that appears to be closely related to Exodus/MIP-3α-LARC, sharing 31% amino acid identity and the same unique Asp-Cys-Cys-Leu motif seen around the first two cysteines. [Hromas et al., *J. Immunol.*, 159:2554–2558 (1997).]

Chemokines of the C—C subfamily have been shown to possess utility in medical imaging, e.g., for imaging the site of infection, inflammation, and other sites having C—C chemokine receptor molecules. See, e.g., Kunkel et al., U.S. Pat. No. 5,413,778, incorporated herein by reference. Such methods involve chemical attachment of a labelling agent (e.g., a radioactive isotope) to the C—C chemokine using art recognized techniques (see, e.g., U.S. Pat. Nos. 4,965,392 and 5,037,630, incorporated herein by reference), administration of the labelled chemokine to a subject in a pharmaceutically acceptable carrier, allowing the labelled chemokine to accumulate at a target site, and imaging the labelled chemokine in vivo at the target site. A need in the art exists for additional new C—C chemokines to increase the available arsenal of medical imaging tools.

More generally, due to the importance of chemokines as mediators of chemotaxis and inflammation, a need exists for the identification and isolation of new members of the chemokine family to facilitate modulation of inflammatory and immune responses. For example, substances that promote the immune response may promote the healing of wounds or the speed of recovery from infectious diseases such as pneumonia. Substances that inhibit the pro-inflammatory effects of chemokines may be useful for treating pathological conditions mediated by inflammation, such as arthritis, Crohn's disease, and other autoimmune diseases.

Additionally, the established correlation between chemokine expression and inflammatory conditions and disease states provides diagnostic and prognostic indications for the use of chemokines, as well as for antibody substances that are specifically immunoreactive with chemokines; a need exists for the identification and isolation of new chemokines to facilitate such diagnostic and prognostic indications.

For all of the aforementioned reasons, a need exists for recombinant methods of production of newly discovered chemokines, which methods facilitate clinical applications involving the chemokines and/or chemokine inhibitors.

SUMMARY OF THE INVENTION

The present invention fulfills one or more of the needs outlined above by providing purified and isolated polynucleotides encoding a human C—C chemokine designated Exodus, and fragments and analogs thereof; purified and isolated Exodus polypeptides, fragments and analogs thereof; materials and methods for the recombinant production of these polypeptides, fragments, and analogs thereof; antibodies to such Exodus polypeptides and analogs; pharmaceutical compositions comprising these polypeptides, fragments, analogs, or antibodies; and treatments using these polypeptides, fragments, analogs, or antibodies, including prophylactic and therapeutic treatment.

Exodus is a member of the C—C chemokine family that is expressed preferentially in lymphocytes and monocytes, and is markedly up-regulated by inflammatory stimuli. The deduced amino acid sequence of the cDNA encoding Exodus is ninety-five amino acids in length, of which the first twenty-two N-terminal residues comprise a signal sequence. Its biological activities as demonstrated herein are expected to render it useful in a number of different clinical applications. Like other C—C chemokines, it stimulates chemotaxis of mononuclear cells. Significantly, Exodus inhibits hematopoietic progenitor cell proliferation and also inhibits HIV production in infected cells.

The invention specifically provides: purified polynucleotides (i.e., DNA and RNA, both sense and antisense strands) encoding the Exodus amino acid sequence of SEQ ID NO: 2, particularly a DNA comprising a nucleotide sequence consisting of the Exodus protein-coding portion (nucleotides 43 to 327) of the nucleotide sequence of SEQ ID NO: 1; purified polynucleotides encoding amino acids 1 to 73 of SEQ ID NO: 2, particularly a DNA comprising a nucleotide sequence consisting of nucleotides 109 to 327 of SEQ ID NO: 1; and purified polynucleotides encoding a full-length Exodus selected from the group consisting of: (a) nucleotides 43 to 327 of the DNA of SEQ ID NO: 1; (b) a polynucleotide which hybridizes under stringent conditions to the complementary strand of nucleotides 43 to 327 of the DNA of SEQ ID NO: 1 or which would hybridize thereto tinder stringent conditions but for the degeneracy of the genetic code; and (c) a polynucleotide which encodes the same Exodus polypeptide as nucleotides 43 to 327 of the DNA of SEQ ID NO: 1. The invention also provides vectors comprising such polynucleotides, particularly expression vectors where DNA encoding Exodus is operatively linked to an expression control DNA sequence, host cells stably transformed or transfected with such polynucleotide DNA, and corresponding methods for producing Exodus by culturing these host cells and isolating the Exodus from the host cells or their nutrient medium. The invention further provides purified Exodus polypeptides, particularly a polypeptide comprising the amino acid sequence of SEQ ID NO: 2, or a polypeptide comprising amino acids 1 to 73 of SEQ ID NO: 2. Another aspect of the invention provides antibodies specifically reactive with Exodus, including monoclonal antibodies and hybridoma cell lines producing such monoclonal antibodies.

Yet a further aspect of the invention provides a method of increasing resistance to HIV infection by administering to a subject an amount of Exodus protein product effective to inhibit HIV proliferation, particularly where the subject is at risk of exposure to HIV, or has been exposed to HIV, or has been infected with HIV. This aspect of the invention also provides a method of treating HIV infection comprising administering to a subject infected with HIV an amount of Exodus protein product effective to inhibit HIV proliferation. A further aspect of the invention provides a method of protecting bone marrow progenitor cells from cytotoxic effects comprising administering an amount of Exodus protein product effective to suppress bone marrow progenitor cell proliferation, particularly where the subject is undergoing chemotherapy or radiotherapy. Yet a further aspect of the invention provides a method of treating myeloproliferative diseases comprising administering an amount of Exodus protein product effective to suppress malignant bone marrow progenitor cell proliferation. The invention is described more fully below.

The invention provides purified and isolated polynucleotides (i.e., DNA and RNA, both sense and antisense strands) encoding Exodus. Preferred DNA sequences of the invention include genomic and cDNA sequences and chemically synthesized DNA sequences.

The nucleotide sequence of a cDNA encoding this Exodus chemokine, including 5' and 3' non-coding sequences, is set forth in SEQ ID NO: 1. Nucleotides 43 to 327 comprise the Exodus protein coding portion of this DNA of SEQ ID NO: 1, and a preferred DNA of the present invention comprises nucleotides 109 to 327 of SEQ ID NO: 1, which comprise the putative coding sequence of the mature, secreted Exodus protein without its signal sequence.

The amino acid sequence of chemokine Exodus is set forth in SEQ ID NO: 2. Preferred polynucleotides of the present invention include, in addition to those polynucleotides described above, polynucleotides that encode the amino acid sequence set forth in SEQ ID NO: 2, and that differ from the polynucleotides described in the preceding paragraphs only due to the well-known degeneracy of the genetic code.

Similarly, since twenty-two amino acids (positions −22 to −1) of SEQ ID NO: 2 comprise a signal peptide that is cleaved to yield the mature Exodus chemokine, preferred polynucleotides include those which encode amino acids 1 to 73 of SEQ ID NO: 2. Thus, a preferred polynucleotide is a purified polynucleotide encoding a polypeptide having an amino acid sequence comprising amino acids 1 to 73 of SEQ ID NO: 2.

Among the uses for the polynucleotides of the present invention is the use as hybridization probes, to identify and isolate genomic DNA encoding human Exodus, which gene is likely to have a three exon/two intron structure characteristic of C—C chemokines genes (See Baggiolini et al., supra); to identify and isolate non-human genes encoding proteins homologous to Exodus, to identify human and non-human chemokines having similarity to Exodus; and to identify those cells which express Exodus and the conditions under which this protein is expressed.

Thus, in another aspect, the invention provides a purified polynucleotide which hybridizes under stringent conditions to the complementary strand of the Exodus coding portion of the DNA of SEQ ID NO: 1. Similarly, the invention provides a purified polynucleotide which, but for the redundancy of the genetic code, would hybridize under stringent conditions to the complementary strand of the Exodus coding portion of the DNA of SEQ ID NO: 1. Exemplary stringent hybridization conditions are as follows: hybridization at 42° C. in 5×SSC, 20 mM NaPO$_4$, pH 6.8, 50% formamide; and washing at 42° C. in 0.2×SSC. Those skilled in the art understand that it is desirable to vary these conditions empirically based on the length and the GC nucleotide base content of the sequences to by hybridized, and that formulas for determining such variation exist. [See, e.g., Sambrook et al., *Molecular Cloning: a Laboratory Manual.* Second Edition, Cold Spring Harbor, N.Y.: Cold Spring Harbor Laboratory (1989).]

In another aspect, the invention includes plasmid and viral DNA vectors incorporating DNAs of the invention, including any of the DNAs described above. Preferred vectors include expression vectors in which the incorporated Exodus-encoding cDNA is operatively linked to an endogenous or heterologous expression control sequence. Such expression vectors may further include polypeptide-encoding DNA sequences operably linked to the Exodus-encoding DNA sequences, which vectors may be expressed to yield a fusion protein comprising the Exodus polypeptide of interest.

In another aspect, the invention includes a prokaryotic or eukaryotic host cell stably transfected or transformed with a DNA or vector of the present invention. In preferred host cells, the Exodus polypeptide encoded by the DNA or vector of the invention is expressed. The DNAs, vectors, and host cells of the present invention are useful, e.g., in methods for the recombinant production of large quantities of Exodus polypeptides of the present invention. Such methods are themselves aspects of the invention. For example, the invention includes a method for producing Exodus wherein a host cell of the invention is grown in a suitable nutrient medium and Exodus protein is isolated from the cell or the medium.

In yet another aspect, the invention includes purified and isolated Exodus polypeptides. A preferred peptide is a purified chemokine polypeptide having an amino acid sequence comprising amino acids 1 to 73 of SEQ ID NO: 2. The polypeptides of the present invention may be purified from natural sources, but are preferably produced by recombinant procedures, using the DNAs, vectors, and/or host cells of the present invention, or are chemically synthesized. Purified polypeptides of the invention may be glycosylated (e.g., O-linked or N-linked) or non-glycosylated, water soluble or insoluble, oxidized, reduced, etc., depending on the host cell selected, recombinant production method, isolation method, processing, storage buffer, and the like. Alternatively, Exodus polypeptides may be prepared by chemical peptide synthesis using techniques that have been used successfully for the production of other chemokines such as IL-8 [Clark-Lewis et al., *J. Biol Chem.*, 266:23128–34 (1991)] and MCP-1.

The invention also contemplates Exodus polypeptide fragments, wherein one or more N-terminal or C-terminal amino acid residues are deleted, and which retain one or more of the biological activities characteristic of the C—C chemokines.

Another aspect of the invention includes Exodus polypeptide analogs wherein one or more amino acid residues is added, deleted, or replaced from the Exodus of the present invention, and which retain one or more of the biological activities characteristic of the C—C chemokines. Such analogs are useful for, e.g., the medical imaging methods described above or the treatment methods described below. They may be prepared by any recombinant or synthetic methods known in the art, including those described below in Example 7.

Exemplary analogs include substitutions in the Exodus amino acid sequence designed to effect greater homology with the chemokines to which it is most closely related. Substitutions designed to effect greater homology with the C—C chemokine family include replacing the alanine at position 31 in the mature protein sequence with a threonine, or replacing the phenylalanine at position 26 with a tyrosine. Other substitutions that would effect greater homology with MIP-1α, MIP-1β and RANTES include replacing residues 1–8 of Exodus with residues 1–10 of MIP-1α or residues 1–9 of RANTES, replacing the leucine at position 11 with a phenylalanine, replacing the glycine at position 12 with a serine, replacing the glycine at position 25 with a glutamic acid, replacing the glutamic acid at position 36 with a serine, replacing the serine at position 46 with a glutamine, replacing the isoleucine at position 60 with a tyrosine, and replacing the serine at position 67 with an aspartic acid. These substitutions may be made singly or in all combinations, and are expected to have a potential for enhancing the activity of Exodus in myelosuppression or inhibition of HIV production.

Other substitutions designed to enhance the properties of an amino acid at a given position (e.g., if an amino acid is hydrophobic, the replacement is to be more hydrophobic) may also enhance the activities of Exodus: replacing the asparagine at position 6 with an aspartic acid, replacing the leucine at position 18 with an isoleucine, replacing the glutamine at position 29 with a glutamic acid, replacing the asparagine at position 38 with aspartic acid, replacing the valine at position 50 with isoleucine, and replacing the glutamine at position 56 with glutamic acid. These substitutions may be made singly or in all combinations.

A related aspect of the invention includes analogs which lack the biological activities of Exodus, but which are capable of competitively or non-competitively inhibiting the binding of C—C chemokines with their receptor(s). Such analogs are useful, e.g., in therapeutic compositions or methods for inhibiting the biological activity of endogenous Exodus or other C—C chemokines in a host. Such Exodus polypeptide analogs are specifically contemplated to modulate the binding characteristics of Exodus to chemokine receptors and/or other molecules (e.g., heparin, glycosaminoglycans, erythrocyte chemokine receptors) that are considered to be important in presenting Exodus to its receptor.

In related aspects, the invention provides purified and isolated polynucleotides encoding such Exodus polypeptide analogs, which polynucleotides are useful for, e.g., recombinantly producing the Exodus polypeptide analogs; plasmid and viral vectors incorporating such polynucleotides; and prokaryotic and eukaryotic host cells stably transformed with such DNAs or vectors.

In another aspect, the invention includes antibody substances (e.g., monoclonal and polyclonal antibodies, single chain antibodies, chimeric or humanized antibodies, and the like) which are specifically immunoreactive with Exodus polypeptides and polypeptide analogs of the invention. The invention further includes hybridoma cell lines that produce antibody substances of the invention. Such antibodies are useful, for example, for purifying polypeptides of the present invention, for detection or quantitative measurement of Exodus in fluid or tissue samples, e.g., using well-known ELISA techniques, and for modulating binding of Exodus to its receptor(s). Some chemokine antibodies (e.g., anti-IL-8 antibodies) have been shown to have dramatic anti-inflammatory effects.

Recombinant Exodus polypeptides and polypeptide analogs of the invention may be utilized in place of antibodies in binding reactions, to identify cells expressing receptor(s) of Exodus and in standard expression cloning techniques to isolate polynucleotides encoding the receptor(s). See, e.g., Example 16 below and the cloning of the IL-8 and MCP-1 receptors in Holmes et al., supra, and Charo et al., supra, respectively. Such Exodus polypeptides, Exodus polypeptide analogs, and Exodus receptor polypeptides are useful for modulation of Exodus chemokine activity, and for identification of polypeptide and chemical (e.g., small molecule) Exodus agonists and antagonists.

As used herein, "Exodus protein product" includes Exodus polypeptides, fragments, or analogs thereof, including alternatively spliced variants of Exodus, such as the chemokine Ckβ-4 described in International Publication No. WO 96/05856, supra, that retain the relevant biological activities of Exodus. We have demonstrated that the extra alanine found in Ckβ-4 (after residue 4 of Exodus) falls at an intron-exon boundary. Sequencing across this region suggests that these two forms of Exodus arise by alternative splicing.

The invention also contemplates pharmaceutical compositions comprising Exodus protein products for use in methods for enhancing the immune response in a mammal suffering from a wound or an infectious disease. Also contemplated are pharmaceutical compositions comprising Exodus protein products or antibodies thereto, for use in methods for reducing inflammation in inflammation-mediated pathological conditions, such as arthritis, Crohn's disease, or other autoimmune diseases. Further contemplated are pharmaceutical compositions for use in reducing atherosclerosis, angiogenesis or tumor growth or metastasis.

Particularly contemplated are pharmaceutical compositions for use in suppressing proliferation of hematopoietic stem or progenitor cells. Such myelosuppression may protect stem/progenitor cells against cytotoxic effects during chemotherapy or radiotherapy. Also contemplated is use of an Exodus protein product for manufacture of a medicament for suppressing bone marrow progenitor cell proliferation, said medicament being particularly desirable for administration to a subject undergoing chemotherapy or radiotherapy.

Also particularly contemplated are pharmaceutical compositions for use in treating myeloproliferative diseases, and use of an Exodus protein product for manufacture of a medicament for treating myeloproliferative diseases.

Further particularly contemplated are pharmaceutical compositions for use in the treatment of patients recently exposed to HIV, but not yet tested for or confirmed to be HIV-positive by standard diagnostic procedures (e.g., neonates from HIV-positive mothers, medical personnel exposed to HIV-positive blood), patients at risk of exposure to HIV, or patients already infected with HIV, i.e., HIV-positive patients. Also contemplated is use of an Exodus protein product for manufacture of a medicament for inhibiting HIV proliferation, said medicament being particularly desirable for administration to subjects at risk of exposure to HIV, or exposed to HIV, or infected with HIV. Further contemplated is use of an Exodus protein product for manufacture of a medicament for treating HIV infection.

Such pharmaceutical compositions comprise Exodus protein product, or an antibody thereto, with a physiologically acceptable diluent or carrier, and may optionally include other appropriate therapeutic agents depending on the clinical application, e.g., anti-inflammatory agents or anti-HIV agents. Dosages of Exodus protein product will vary between about 1 μg to 100 mg/kg body weight, preferably 5 to 100 μg/kg body weight, depending on the pathological condition to be treated. Such phamaceutical compositions may be administered by a variety of routes depending on the condition to be treated, including via subcutaneous, intramuscular, intravenous, intrapulmonary, transdermal, intrathecal, oral, or suppository administration.

The doses of the Exodus protein product may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels for the treatment of various diseases and conditions.

The Exodus materials and methods described above may be employed in several clinical applications. First, as chemokines attract and activate monocytes and macrophages (Baggiolini et al., supra), Exodus expression in a pathogenic inflammatory setting may exacerbate the disease by recruiting additional monocytes and macrophages or other leukocytes to the disease site, by activating the leukocytes that are already there, or by inducing leukocytes to remain at the site. Thus, inhibiting the chemoattractant activity of Exodus may be expected to alleviate deleterious inflammatory processes. Significantly, the potential benefits of such an approach have been directly demonstrated in experiments involving IL-8, a C-X-C chemokine that attracts and activates neutrophils. Antibodies directed against IL-8 have a profound ability to inhibit inflammatory disease mediated by neutrophils [Harada et al., *J. Leukoc. Biol.*, 56:559 (1994)]. Inhibition of Exodus is expected to have a similar effect in diseases in which monocytes or macrophages are presumed to play a role, e.g., Crohn's disease, rheumatoid arthritis, atherosclerosis, myocardial infarction, or acute respiratory distress syndrome (ARDS).

Alternatively, augmenting the effect of Exodus may have a beneficial role in diseases, as chemokines have also been shown to have a positive effect in wound healing and angiogenesis. Thus, exogenous Exodus protein products or Exodus agonists may be beneficial in promoting recovery from such diseases.

Exodus protein products or Exodus agonists may also prove to be clinically important in the treatment of tumors, as suggested by the ability of the C—C chemokine TCA3 to inhibit tumor formation in mice (see Laning et al., supra). Exodus may act directly or indirectly to inhibit tumor formation, e.g., by attracting and activating various non-specific effector cells to the tumor site or by stimulating a specific anti-tumor In addition, the myelosuppressive effect demonstrated herein for Exodus indicates that Exodus protein products or Exodus agonists may yield substantial benefits for patients receiving chemotherapy or radiation therapy, reducing the deleterious effects of the therapy on the patient's myeloid stem or progenitor cells. For example, treatment with Exodus protein product before or during (e.g. a day before, immediately before, or at the same time as) administration of cell cycle-specific chemotherapeutic agents may protect the bone marrow against the cytotoxic effects of the agents. Such cell cycle-specific chemotherapeutic agents include vinblastine, etoposide, daunoribicin, doxorubicin, idarubicin, methotrexate, hydroxyurea, fluorouracil, cytosine arabinoside, mercaptopurine, thioguanine, pentostatin, fludarabine, and 2-chlorodeoxyadenosine (2-CDA). As discussed above, a MIP-1α analog (designated BB10010, British Biotechnology) is currently in clinical trials as a myeloprotective agent in Cytoxan® therapy (cyclophosphamide from Bristol-Myers Squibb Oncology).

The ability of Exodus to inhibit proliferation of cytokine-dependent myeloid cell lines, as shown herein, indicates that Exodus protein product will also be useful in treating myeloproliferative diseases, including but not limited to chronic myclogenous leukemia, essential thrombocytosis, myelofibrosis, and polycythemia vera. Administration of Exodus protein product for this purpose may be concurrent with administration of other chemotherapeutic agents or other cytokines, such as interferon.

Furthermore, the C—C chemokines RANTES, MIP-1α and MIP-1β have been shown to suppress replication of human immunodeficiency virus HIV-1 [Cocchi et al., *Science*, 270:1811–1815 (1995)], implicating them as possible therapeutic agents in the prevention or treatment of AIDS. The ability of Exodus to inhibit HIV proliferation, as demonstrated herein, indicates that Exodus protein product will also be beneficial for treating AIDS patients, in preventing onset or progression of AIDS, or in promoting resistance to HIV infection after HIV exposure. Full-blown AIDS does not appear immediately upon infection with HIV; there is a variable period of time during which the patient remains healthy but exhibits viremia. This viremia is sustained by continuous rounds of viral replication and reinfection of blood cells. One study has found that measurements of plasma viral load (as well as CD4 lymphocyte counts) can predict the subsequent risk of AIDS or death. [Ho, *Science*, 272:1124–1125 (1996).] Interference with the continuous cycle of viral replication may therefore result in an improved prognosis.

Additionally, the established correlation between chemokine expression and inflammatory conditions and disease states provides diagnostic and prognostic indications for the use of Exodus protein products, including antibody substances that are specifically immunoreactive with Exodus. Such Exodus materials are useful in methods for diagnosing and assessing the prognosis of inflammatory conditions and disease states, as well as for medical imaging of areas involved in such conditions and disease states.

Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1:
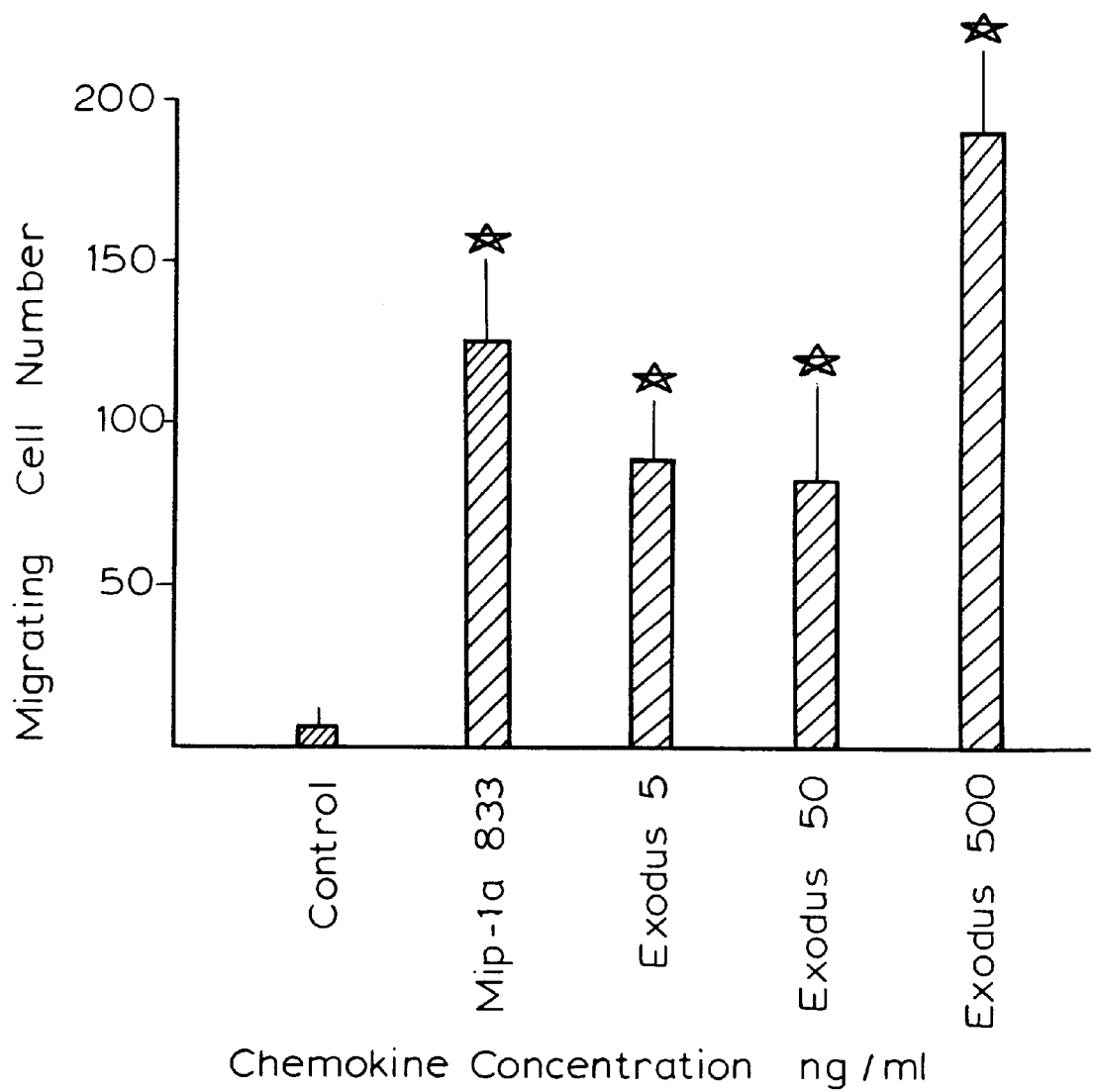
FIG. 1 shows the effect of varying concentrations of Exodus on mononuclear cell chemotaxis.

The invention is based upon the identification of a cDNA sequence encoding Exodus and characterization of the activities of Exodus.

The complete cDNA of the chemokine Exodus is 821 nucleotides in length. There is a consensus polyadenylation site at 786. The 3' untranslated sequence has a number of AAAU sequences that mediate mRNA stability in many cytokine genes. These sequences promote message degradation, and contribute to the short half life of many cytokine transcripts, including chemokines. There is a short 5' untranslated region of 43 nucleotides.

There are 95 amino acids in the deduced amino acid sequence of Exodus. This is consistent with the C—C chemokine family, where the length of family members ranges from 91 to 99. The first 22 amino acids of Exodus constitute a strongly hydrophobic signal peptide. The four cysteines that participate in the disulfide bonds that define this family are also conserved in Exodus. Exodus is most closely related to MIP-1α and RANTES at the amino acid level, with 26–28% identity, and about 75% similarity when conservative changes are taken into account. Exodus is especially similar to RANTES from amino acids 24 to 46 and again from 58 to 75, where between these positions there are only six non-conservative changes.

While Exodus has many of the conserved amino acid features of the other human C—C chemokines, there are several unusual characteristics of Exodus that are worth noting. Exodus has a highly basic carboxy-terminus, more consistent with the MCP sub-family than RANTES. In addition, Exodus lacks a conserved tyrosine and a threonine at position 47 and 51, respectively, that are present in all other human C—C chemokines, including RANTES. It is not clear if these two highly conserved amino acids play a role in C—C chemokine activity since they are not predicted to contact the receptor.

Various aspects and advantages of the present invention will be understood upon consideration of the following illustrative examples. Example 1 describes the identification of Exodus cDNA. Example 2 describes experiments examining the pattern of Exodus gene expression in various human cell lines and tissues. Example 3 describes the recombinant expression of the Exodus gene in mammalian cells. Example 4 describes another method for recombinant expression of the Exodus gene in mammalian cells, and purification of the resulting protein. Example 5 provides a protocol for expression of the Exodus gene in prokaryotic cells and purification of the resulting protein. Example 6 provides a protocol for the recombinant production of Exodus in yeast or invertebrate cells. Example 7 describes production of Exodus and Exodus analogs by peptide synthesis or recombinant production methods. Example 8 provides a protocol for generating monoclonal antibodies that are specifically immunoreactive with Exodus. Example 9 addresses the effect of Exodus on monocyte chemotaxis in vitro. Example 10 addresses the effect of Exodus on the proliferation of myeloid progenitor cells, myeloid cell lines and chronic myelogenous leukemia progenitor cells. Example 11 addresses the effect of Exodus on HIV p24 protein production. Examples 12, 13, 14 and 15 provide in vivo assays of chemoattractant and leukocyte activation, tumor growth inhibition, and leukocyte activation after intraperitoneal or subcutaneous injection. Example 16 describes cloning of an Exodus receptor.

EXAMPLE 1

Identification of the cDNA Sequence Encoding Exodus

As described in Takeda et al., *Human Mol. Genetics*, 2:1793–1798 (1993), messenger RNA was prepared from dissected normal adult human pancreatic islet cells, and first strand cDNA was synthesized by oligo(dT) priming using a primer that contained an XhoI site. After second strand cDNA synthesis and blunting, EcoRI adapters were ligated to the cDNA, which was then size-fractionated to remove products of less than 1000 base pairs in size. After XhoI digestion, the products were cloned into lambda ZAP II, and amplified in XL1-Blue MRF' cells (Stratagene, La Jolla, Calif.). The library was converted to plasmids by rescuing pBluescript SK—according to the manufacturer's instructions. Partial sequences of 1000 of these randomly isolated pancreatic islet cDNAs were determined by single-pass automated sequencing. These sequences deposited in GenBank (Takeda et al., supra) and were compared with other sequences in the National Center for Biotechnology Information (NCBI) database. The average length of the cDNA sequences used for comparison was approximately 200 bp. This work was published in Takeda et al., supra.

Subsequent to the work of Takeda et al., a clone encoding Exodus was identified among these 1000 pancreatic islet Expressed Sequence Tags (ESTs) as follows. Comparison of a consensus chemokine sequence against these ESTs using the BLAST service of NCBI revealed that one of the clones possessed a distant homology to the C—C chemokine family. This homology to the chemokine family increased after several sequencing errors from the original automated pass were identified by manual dideoxy double stranded sequencing, and the coding region and reading frame was properly characterized. This clone, originally designated HBC2850 by Takeda et al., was not identical to any other known chemokine. The cDNA in this clone consisted of 821 nucleotides, which contain the entire open reading frame of the chemokine protein. This chemokine was designated Exodus.

The differences between the Exodus cDNA sequence, set forth in SEQ ID NO: 1, and the EST sequence of Takeda et al. are as follows (with references to nucleotide numbering according to SEQ ID NO: 1): at nucleotide 64 ("C" in Exodus), the EST nucleotide was "N"; at nucleotide 71 ("C" in Exodus), the EST nucleotide was "N"; between nucleotides 130 and 131, the EST contained an extra "G" base which caused a shift in the reading frame; between nucleotides 150 and 151, the EST contained an extra "T" base which caused a shift in the reading frame; at nucleotide 193 ("C" in Exodus), the EST nucleotide was "N"; at nucleotide 196 ("C" in Exodus), the EST nucleotide was "N"; at nucleotide 271 ("A" in Exodus), the EST nucleotide was "N"; and at nucleotide 309 ("T" in Exodus), the EST nucleotides were "GC".

EXAMPLE 2

Exodus Gene Expression Pattern in Cell Lines and Tissues

The pattern of Exodus mRNA expression was examined through Northern blotting of mRNA extracted from various human tissues and cell lines. The probe used was the cDNA containing the complete coding region of Exodus, isolated by agarose gel electrophoresis, and labeled with $^{32}$P-dCTP and $^{32}$P-dTTP (DuPont-NEN, Boston, Mass.) by random priming according to the manufacturer's instructions (BMB, Indianapolis, Ind.).

A. Exodus Gene Expression in Human Tissues

RNA was isolated from cell lines and cultured monocytes using RNA STAT-60 (Tel-Test B Inc., Friendswood, Tex.) according to the manufacturer's instructions. Total RNA (20 µg) was fractionated on 0.8% formaldehyde agarose gels, transferred to nitrocellulose, hybridized and washed under stringent conditions. The films were exposed for one day with an intensifying screen at −80° C.

A Human Multiple Tissue Northern blot and a Human Immune System Multiple Tissue Northern (Clontech, Palo Alto, Calif.) were also probed with the Exodus cDNA and washed under stringent conditions according to the manufacturer's instructions. The autoradiograph was exposed as above for 1–4 days.

Exodus appeared to have a very restricted pattern of expression. It was not expressed in a number of cell lines tested, including TMR323 neuroblastoma, MDA breast carcinoma, K562 erythroleukemia, Jurkat T-cell leukemia, HL60 promyelocytic leukemia, HL60 cells differentiated to granulocytes with retinoic acid, 3T3 embryonic fibroblasts, or 293 embryonic kidney cells. When a commercially-prepared Northern blot of a variety of normal human tissues was analyzed for Exodus expression, expression was detected in the lung, and not in heart, brain, placenta, adult liver, skeletal muscle, kidney, pancreas, spleen or bone marrow. The size of the transcript was approximately 0.9 kB, consistent with the size of the cDNA reported here, given the addition of a poly A tail.

However, when a commercially-prepared Northern blot of lymphoid tissues was examined for Exodus expression, it was found to be highly expressed in several different lymphoid organs. Exodus was highly expressed in peripheral lymph nodes, appendix, peripheral blood mononuclear cells, and fetal liver. It was less highly expressed in the thymus, and there was no detectable expression in the spleen or marrow.

This expression pattern is typical of many chemokines. Exodus was expressed mainly in lymphoid tissue, especially in lymph nodes, the appendix, and peripheral blood. It is possible that the lymphoid tissue used in this Northern blot analysis may have been activated by some immunologic stimulus, thus causing a higher than usual level of expression of Exodus. The poor expression of Exodus in bone marrow as opposed to peripheral blood may be due to the fact that the bone marrow is mainly composed of immature myeloid and erythroid precursors, while there are far more mature mononuclear cells in the peripheral blood.

B. Exodus Gene Expression After Inflammatory Stimulus

Since the expression of many chemokines is induced in mononuclear cells by inflammatory stimuli, the expression of Exodus after exposure of various cell lines to LPS, TNF-alpha, or PMA was analyzed by Northern blot analysis.

The monocytic cell line THP-1 was obtained from American Type Culture Collection (Rockville, Md.). Cells were maintained in RPMI 1640 media (Biowhitaker, Walkersville, Md.) supplemented with 10% fetal calf serum (FCS, Hyclone Laboratories, Inc., Logan, Utah), 25 mM HEPES, 100 U/ml penicillin and 100 μg/ml streptomycin (tissue culture antibiotics, Life Technologies, Gaithersburg, Md.). For stimulation experiments cells were cultured at a density of one million cells per ml in the presence of phorbol ester (PMA, Sigma, St. Louis, Mo.).

The immortalized human umbilical vein endothelial cell line I-HUVEC was obtained from Dr. Jay Nelson, University of Oregon, and cultured in RPMI 1640 supplemented with 10% FCS (Hyclone), 400 ug/ml G418 (Life Technologies, Grand Island, N.Y.), 1 u/ml heparin (Sigma), and 30 μg/ml endothelial cell growth factor (Collaborative Biomedical Products, Bedford, Mass.) to a confluency of 70–80%, then cultured in the presence or absence of 10 ng/ml tumor necrosis factor-alpha (TNF-α, Peprotech, N.J.) for various periods of time.

Peripheral blood mononuclear cells were purified on Histopaque gradients (Sigma) and monocytes were isolated by plastic adherence. Monocytes were cultured for 6 days, with media being replaced every two days to allow for differentiation into macrophages. Cells were stimulated with 100 ng/ml lipopolysacharide (LPS, Sigma) for various time periods.

Exodus expression was highly induced when peripheral blood mononuclear cells were exposed to LPS for 8 or 12 hours. Exodus expression was again highly induced when umbilical vein endothelial cells were exposed to TNF-α for only three hours. Significantly, Exodus expression stayed high as long as there was the inflammatory stimuli present, When the monocytic leukemia cell line THP-1 was treated with PMA the expression of Exodus was also induced, reaching its peak at 48 hours after exposure, and declining slightly thereafter.

These results indicated that Exodus was poorly expressed unless inflammatory stimuli were present. However, once such a stimulus was present Exodus was rapidly and stably up-regulated. The nature of the stimulus itself also seemed unrestricted, with LPS,TNF-α, and PMA all up-regulating Exodus. Exodus production thus appears to be a function of a mature lymphophagocytic cell, especially after inflammatory stimuli, and not of immature myeloid cells.

EXAMPLE 3

Production of Recombinant Exodus in COS Cells

Recombinant Exodus was produced by transiently transfecting the Exodus cDNA into COS cells. The full length Exodus cDNA was subcloned using common restriction sites into the polylinker site of pECE [Ellis et al., CELL, 45:721 (1986)] an SV-40-driven expression vector, in sense orientation. Log phase COS cells (American Type Culture Collection (ATCC) No. CRL 1651) were plated in DMEM with 10% FCS (Hyclone) and 100 U/ml penicillin and 100 μg/ml streptomycin (tissue culture antibiotics, Life Technologies, Gaithersburg, Md.) at a density of one million cells per 100 mm culture dish and incubated overnight. Twenty μg of purified pECE-Exodus plasmid DNA per plate was used for transfection of the COS cells with Lipofectin per the manufacturer's instructions (Life Technologies, Bethesda, Md.). Purified pECE plasmid (without Exodus DNA) was transfected identically into COS cells to serve as a control. An expression vector with the reporter gene beta-galactosidase (SV40/beta-Gal, Phannacia, Piscataway, N.J.) was co-transfected to control for transfection efficiencies. Seventy-two hours later, the supernatant of the COS cell culture was filtered through 0.2 μm filters and stored at −70° C. After supernatant removal, cell lysates were made and beta galactosidase activity assayed as previously described in Rosenthal, Meth. Enzymol., 152:704 (1987). When pECE and pECE-Exodus transfections were performed, side-by-side tranfection efficiencies as determined by beta-galactosidase activity were within 10% of each other.

EXAMPLE 4

Production of Recombinant Exodus in CHO Cells and Purification Thereof

PCR was used to amplify bases 30 to 330 of the Exodus cDNA (shown in SEQ ID NO: 1), which includes 13 bp of 5' non-coding and 3 bp of 3' non-coding sequence. The sequences of the PCR primers were: 5'-GGCGAAGCTTTGAGCTAAAAACCATG (SEQ ID NO: 3) and 5'-GCGGGAATTCTTACATGTTCTTGACT (SEQ ID NO: 4). To facilitate cloning, these primers include HindIII and EcoRI restriction sites, respectively (shown in italics). The fragment was cloned into the vector pDCI (described in co-owned, co-pending U.S. patent application Ser. No. 08/558,658 filed Nov. 16, 1995, hereby incorporated by reference), which is a pBR322 derivative which contains the CMV immediate early promoter adjacent to the cloning site to facilitate expression of the insert, and the also contains the bacterial beta-lactamase gene and the murine dihydrofolate reductase (DHFR) gene to allow selection of the plasmid in bacterial and mammalian cells, respectively (Sambrook et al., supra). The construct containing the Exodus insert was linearized by restriction digestion with PvuI (BMB, Indianapolis, Ind.), which cleaves within the vector sequence. The linearized plasmid was precipitated with ethanol and redissolved in HBS (20 mM HEPES-NaOH, pH 7.0; 137 mM NaCl, 5 mM KCl; 0.7 mM $Na_2HPO_4$; 6mM Dextrose). For electroporation, $10^7$ cells of the CHO cell line DG44 [Urlab et al., Cell, 33:405 (1983)], were washed, resuspended in 1 ml PBS, mixed with 10 micrograms of linearized plasmid, and transferred to a 0.4 cm electroporation cuvette. The suspension was electroporated with a Biorad Gene Pulser (Richmond, Calif.) at 290 volts, 960 µFarad. Transformants were selected by growth in DMEM/F12 medium (Gibco) containing 10% dialyzed FCS (Hyclone, Logan, Utah) and lacking hypoxanthine and thymidine. Cells from several hundred transformed colonies were pooled and replated in DMEM/F12 medium containing 20 nM methotrexate (Sigma, St. Louis, Mo.). Colonies surviving this round of selection were isolated and expanded to obtain individual clones. The level of Exodus expression was determined as follows.

Clones were grown on tissue culture plates to approximately 90% confluence in DMEM/F12 medium containing 10% dialyzed FCS, at which time the medium was replaced. The cells were allowed to grow for 4 days in DMEM/F12 medium containing 1% dialyzed FCS. The supernatant was loaded onto a column of Heparin Sepharose CL-6B (Pharmacia, Piscataway, N.J.). The column was washed with 0.2 M NaCl in 20 mM Tris, pH 7.5, and the chemokine was eluted with 0.6 M NaCl in 20 mM Tris, pH 7.5. The eluted Exodus was fractionated by SDS-PAGE through an 18% Tris glycine gel (NOVEX, San Diego, Calif.) and transferred to a PVDF membrane (Millipore, Bedford, Mass.). The Exodus band migrating at approximately 7 kD was confined by detection with rabbit polyclonal antisera specific for Exodus (prepared as described in Example 8 below).

Clones expressing the highest level of Exodus chemokine may be expanded for large scale protein production. The resulting recombinant Exodus is produced and purified from the supernatant as follows. The Exodus band migrating at approximately 7 kD is excised and the N-terminus sequenced on an automated sequencer (Applied Biosystems, Model 473A, Foster City, Calif.).

As a further purification step, the Exodus eluted from the Heparin-Sepharose column is brought to 1.6 M NaCl and loaded onto a column of HI-Propyl 40 micron resin (J. T. Baker, Phillipsburg, N.J.). The column is washed with 1.6 M NaCl in 20 mM Tris, pH 7.5, and the Exodus is eluted with 20 mM Tris, pH 7.5.

The integrity of the eluted Exodus is verified by amino acid analysis to confirm the ratio of the amino acids predicted by the protein sequence and by mass spectrophotometry to confirm the predicted size.

EXAMPLE 5

Production of Recombinant Exodus in Bacteria

Exemplary protocols for the recombinant expression of Exodus in bacteria and purification of the resulting product follow.

The DNA sequence encoding the mature form of the protein is amplified by PCR and cloned into the vector pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR are SEQ ID NO: 4 and 5'-TAT CGG ATC CTG GTT CCG CGT GAA TCA GAA GCA AGC AAC T-3', which includes a BamHI restriction site, a thrombin cleavage site [Chang, Eur. J. Biochem., 151:217 (1985)], and nucleotides 109 to 127 of SEQ ID NO: 1. The resultant PCR product is digested with BamHI and EcoRI and inserted into a pGEX-3X plasmid digested with BglII and EcoRI.

Treatment of the recombinant fusion protein with thrombin or factor Xa (Pharmacia, Piscataway, N.J.) is expected to cleave the fusion protein, releasing the chemokine from the GST portion. The pGEX-3X/Exodus construct is transformed into E. coli XL-1 Blue cells (Stratagene, La Jolla Calif.), and individual transformants were isolated and grown. Plasmid DNA from individual transformants is purified and partially sequenced using an automated sequencer to confirm the presence of the desired Exodus gene insert in the proper orientation.

Induction of the GST/Exodus fusion protein is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate is cleared by sonication, and cell debris is pelleted by centrifugation for 10 minutes at 12,000 ×g. The fusion protein-containing pellet is resuspended in 50 mM Tris, pH 8, and 10 mM EDTA, layered over 50% glycerol, and centrifuged for 30 min. at 6000 ×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/Exodus fusion protein is produced in bacteria as a soluble protein, it may be purified using the GST Purification Module (Pharmacia Biotech).

The fusion protein may be subjected to thrombin digestion to cleave the GST from the mature Exodus protein. The digestion reaction (20–40 µg fusion protein, 20–30 units human thrombin (4000 U/mg (Sigma) in 0.5 ml PBS) is incubated 16–48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of Exodus may be confined by partial amino acid sequence analysis using an automated sequencer (Applied Biosystems Model 473A, Foster City, Calif.).

Alternatively, the DNA sequence encoding the predicted mature Exodus protein may be cloned into a plasmid containing a desired promoter and, optionally, a leader sequence [see, e.g., Better et al., Science, 240:1041–43 (1988)]. The sequence of this construct may be confirmed by automated sequencing. The plasmid is then transformed into E. coli strain MC1061 using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the mature Exodus protein and be cleaved during secretion.

The secreted recombinant protein is purified from the bacterial culture media by the method described above in Example 4 or, e.g., by adapting methods previously described for the purification of recombinantly produced RANTES chemokine [Kuna et al., J. Immunol., 149:636–642 (1992)], MGSA chemokine [Horik et al., J.

*Biol. Chem.* 268:541–46 (1993)], and IP-10 chemokine (expressed in insect cells) [Sarris et al., *J. Exp. Med.*, 178:1127–1132 (1993)].

EXAMPLE 6

Recombinant Production of Exodus in Yeast or Invertebrate Cells

Exemplary protocols for the recombinant expression of Exodus in yeast or invertebrate cells, and for the purification of the resulting recombinant protein follow.

The coding region of the Exodus cDNA is amplified by PCR. A DNA encoding the yeast pre-pro-alpha leader sequence is amplified from yeast genomic DNA in a PCR reaction using one primer containing nucleotides 1–20 of the alpha mating factor gene and another primer complementary to nucleotides 255–235 of this gene [Kurjan and Herskowitz, *Cell*, 30:933–943 (1982)]. The pre-pro-alpha leader coding sequence and Exodus coding sequence fragments are ligated into a plasmid containing the yeast alcohol dehydrogenase (ADH2) promoter, such that the promoter directs expression of a fusion protein consisting of the pre-pro-alpha factor fused to the mature Exodus polypeptide. As taught by Rose and Broach, *Meth. Enz.* 185:234–279, D. Goeddel, ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment [Stearns et al., *Meth. Enz.*, supra, pp. 280–297]. The ADH2 promoter is induced upon exhaustion of glucose in the growth media [Price et al., *Gene*, 55:287 (1987)]. The pre-pro-alpha sequence effects secretion of the fusion protein from the cells. Concomitantly, the yeast KEX2 protein cleaves the pre-pro sequence from the mature Exodus chemokine [Bitter et. al., *Proc. Natl. Acad. Sci. USA*, 81:5330–5334 (1984)].

Alternatively, Exodus is recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted recombinant Exodus is purified from the yeast growth medium by, e.g., the methods used to purify Exodus from bacterial and mammalian cell supernatants (see Examples 4 and 5 above).

Alternatively, the cDNA encoding Exodus is cloned into the baculovirus expression vector pVL1393 (PharMingen, San Diego, Calif.). This Exodus-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Porton 2090 Peptide Sequencer confirms its N-terminal sequence.

EXAMPLE 7

Production of Exodus Analogs

Recombinant techniques such as those described in the preceding examples may be used to prepare Exodus polypeptide analogs. More particularly, polynucleotides encoding Exodus are modified to encode polypeptide analogs of interest using well-known techniques, e.g., site-directed mutagenesis and polymerase chain reaction. See generally Sambrook et al., supra, Chapter 15. The modified polynucleotides are expressed recomnbinantly, and the recombinant polypeptide analogs are purified as described in the preceding examples.

Residues critical for Exodus activity are identified, e.g., by homology to other C—C chemokines and by substituting alanines for the native Exodus amino acid residues. Cysteines are often critical for the functional integrity of proteins because of their capacity to form disulfide bonds. To determine whether any of the four cysteines in Exodus is critical for enzyme activity, each cysteine is mutated individually to a serine.

Other exemplary analogs include substitutions in the Exodus amino acid sequence designed to effect greater homology with the chemokinies to which it is most closely related. Substitutions designed to effect greater homology with the C—C chemokine family include replacing the alanine at position 31 in the mature protein sequence with a threonine, or replacing the phenylalanine at position 26 with a tyrosine. Other substitutions that would effect greater homology with MIP-1α, MIP-1β and RANTES include replacing residues 1–8 of Exodus with residues 1–10 of MIP-1α or residues 1–9 of RANTES, replacing the leucine at position 11 with a phenylalanine, replacing the glycine at position 12 with a serine, replacing the glycine at position 25 with a glutamic acid, replacing the glutamic acid at position 36 with a seine, replacing the serine at position 46 with a glutamine, replacing the isoleucine at position 60 with a tyrosine, and replacing the serine at position 67 with an aspartic acid. These substitutions may be made singly or in all combinations, and are expected to have a potential for enhancing the activity of Exodus in myelosuppression or inhibition of HIV production.

Other substitutions designed to enhance the properties of an amino acid at a given position (e.g., if an amino acid is hydrophobic, the replacement is to be more hydrophobic) may also enhance the activities of Exodus: replacing the asparagine at position 6 with an aspartic acid, replacing the leucine at position 18 with an isoleucine, replacing the glutamine at position 29 with a glutamic acid, replacing the asparagine at position 38 with aspartic acid, replacing the valine at position 50 with isoleucine, and replacing the glutamine at position 56 with glutamic acid. These substitutions may be made singly or in all combinations.

C-terminal deletions are prepared, e.g., by digesting the 3' end of the Exodus coding sequence with exonuclease III for various amounts of time and then ligating the shortened coding sequence to plasmid DNA encoding stop codons in all three reading frames. N-terminal deletions are prepared in a similar manner by digesting the 5' end of the coding sequence and then ligating the digested fragments into a plasmid containing a promoter sequence and an initiating methionine immediately upstream of the promoter site.

These N-terminal deletion analogs may also be expressed as fusion proteins.

Alternatively, Exodus polypeptide analogs may also be prepared by chemical peptide synthesis using techniques that have been used successfully for the production of other chemokines such as IL-8 [Clark-Lewis et al., *J. Biol Chem.*, 266:23128–34 (1991)] and MCP-1. Such methods are advantageous because they are rapid, reliable for short sequences such as chemokines, and allow the selective introduction of novel, unnatural amino acids and other chemical modifications.

The properties of Exodus analogs on one or more types of cells involved in the inflammatory process, (e.g., T lymphocytes, monocytes, macrophages, basophils, eosinophils, neutrophils, mast cells, endothelial cells, epithelial cells or others) are assayed by art-recognized techniques that have been used for assaying such properties of numerous other chemokines. The properties of Exodus analogs on inhibiting myeloproliferation and HIV production are also assayed according to Examples 10 and 11 below.

EXAMPLE 8

Preparation of Antibodies to Exodus

Exodus chemokine was chemically synthesized essentially as described in Example 7. For storage, Exodus was diluted in RPMI medium containing 1% bovine serum albumin (Sigma, St. Louis, Mo.). Exodus was subsequently purified from the medium by passage over a Heparin Sepharose CL-6B column (Pharmacia, Piscataway, N.J.). The column was washed with a solution of 0.2 M NaCl and 20 mM Tris, pH 7.5, and the chemokine was eluted with 0.6 M NaCl and 20 mM Tris, pH 7.5.

To generate polyclonal antisera, 50 $\mu$g of Exodus were emulsified in Freund's Complete Adjuvant for immunization of rabbits. At intervals of 21 days, 50 $\mu$g of Exodus were emulsified in Freund's Incomplete Adjuvant for boosts. These antisera recognized the chemically synthesized Exodus and the CHO cell-derived Exodus (prepared as described in Example 4) on Western blot.

To generate monoclonal antibodies to Exodus, a mouse is injected periodically with recombinant Exodus (e.g., 10–20 $\mu$g emulsified in Freund's Complete Adjuvant) obtained as described in any of Examples 3 through 7. The mouse is given a final pre-fusion boost of Exodus in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 $\mu$g/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice as described in the foregoing paragraph.

One $\times 10^8$ spleen cells are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 $\mu$M sodium hypoxanthine, 0.4 $\mu$M aminopterin, 16 $\mu$M thymidine (HAT) (Gibco), 25 units/ml IL-6 (Boehringer Mannheim) and 1.5× $10^6$ splenocytes/ml and plated into 10 Corning flat-bottom 96-well tissue culture plates (Corning, Corning N.Y.).

On days 2, 4, and 6, after the fusion, 100 $\mu$l of medium is removed from the wells of the fusion plates and replaced with fresh medium. On day 8, the fusion is screened by ELISA, testing for the presence of mouse IgG binding to Exodus as follows. Immulon 4 plates (Dynatech, Cambridge, Mass.) are coated for 2 hours at 37° C. with 100 ng/well of Exodus diluted in 25 mM Tris, pH 7.5. The coating solution is aspirated and 200 ul/well of blocking solution [0.5% fish skin gelatin (Sigma) diluted in CMF-PBS] is added and incubated for 30 min. at 37° C. Plates are washed three times with PBS with 0.05% Tween 20 (PBST) and 50 $\mu$l culture supernatant is added. After incubation at 37° C. for 30 minutes, and washing as above, 50 $\mu$l of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 $\mu$l substrate, consisting of 1 mg/ml o-phenylene diamine (Sigma) and 0.1 $\mu$l/ml 30% $H_2O_2$ in 100 mM Citrate, pH 4.5, are added. The color reaction is stopped after 5 minutes with the addition of 50 $\mu$l of 15% $H_2SO_4$. $A_{490}$ is read on a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

EXAMPLE 9

Effect of Exodus on Monocyte Chemotaxis

The activity of Exodus was evaluated in chemotaxis assays performed as previously described in Martinet et al., *J. Immunol. Meth.*, 174:209, 1994 and Keller et al., *J. Immunol. Meth.*, 1:165, 1972. Twenty ml of peripheral blood was collected from healthy volunteers in 10 ml heparinized tubes. Blood was diluted 1:1 with PBS and then underlaid with 10 ml of Histopaque (Sigma). After centrifugation at 400 g for 25 mins, cells at the interface were collected and washed twice in PBS. Cells were resuspended in DMEM (Life Technologies, Gaithersburg, Md.) with 100 U/ml penicillin and 100 $\mu$g/ml streptomycin (tissue culture antibiotics, Life Technologies) at $10^6$/ml. Sterile bovine serum albumin (Sigma) was added to final concentration of 0.2 mg/ml.

100 $\mu$l of this cell suspension was added to each transwell insert (Costar). DMEM with antibiotics and 0.2% BSA with or without pure synthetic Exodus was added to the lower wells in the 24 well plate. All Exodus concentrations were done in triplicate. Transwell inserts were placed into the lower walls, and incubated at 37° C. for 90 mins. At the completion of the incubation period inserts were removed and the top of the filter scraped with a rubber policeman to remove adherent cells. The entire insert was then stained with Wright-Giemsa. Cells adherent to the lower surface of the insert and those that migrated to the lower well were counted under 3 high power fields, and added together to obtain a total number of migrating cells.

Purified synthetic Exodus was tested at concentrations of 5, 50 and 500 ng/ml. For comparison, MIP-1α was tested at a concentration of 833 ng/ml. The control contained no chemokine. Results are shown in FIG. 1. The values represent the average of two experiments performed in triplicate, plus or minus the standard error. The stars represent statistically significant differences from the control at p<0.05 using the unpaired Student's t-test.

These results show that Exodus stimulated cheinotactic activity of normal human peripheral blood mononuclear cells, as measured by transwell migration. The highest concentrations of Exodus stimulated chemotaxis more efficiently than maximally effective concentrations of MIP-1α.

Similar results were obtained with an Exodus protein product, which was Exodus with an additional alanine after residue 4.

EXAMPLE 10

Effect of Exodus on Proliferation of Myeloid Cells
A. Effect on Myeloid Progenitor Cells The effect of Exodus protein products on hematopoietic colony formation were assayed essentially as previously described in, e.g., Broxmeyer et al., *Blood*, 76:1110 (1990). Bone marrow cells were collected from human donors after obtaining informed consent. Low density human bone marrow cells at $5 \times 10^4$/ml were plated in 1% methylcellulose in Iscove's Modified Essential Medium (Biowhitaker, Walkersville, Md.) supplemented with 30% FCS (Hyclone), recombinant human erythropoietin (EPO, 1 U/ml, Amgen, Thousand Oaks, Calif.), recombinant human interleukin-3 (IL-3, 100 U/ml, Immunex, Seattle, Wash.), and recombinant human stem cell factor (SCF, 50 ng/ml, Amgen) for colony forming unit granulocyte/macrophage (CFU-GM), colony forming unit granulocyte/erythrocyte/macrophage/megakaryocyte (CFU-GEMM) or blast forming unit-erythrocyte (BFU-E) analysis. Cultures were incubated at 5% CO and low oxygen tension (5%) for 14 days, and then scored for colony formation using an inverted microscope in a blinded fashion. Experiments were performed at least twice in triplicate.

Varying amounts of COS cell supernatant containing Exodus, prepared as described in Example 3 above, were tested in this assay, as was MIP-1α (R&D Systems, Minneapolis, Minn.) at 50 ng/ml. Results are shown in Table 1 below, which displays the mean count of hematopoietic progenitor colonies per plate, plus or minus the standard deviation.

TABLE 1

| Chemokine in Medium | CFU-GM | BFU-E | CFU-GEMM |
|---|---|---|---|
| Control (no chemokine) | 53 ± 8 | 56 ± 8 | 24 ± 5 |
| MIP-1α 50 ng/ml | 23 ± 4* | 37 ± 3* | 12 ± 1* |
| Exodus COS cell supernatant (0.2 ml in 2 ml total medium) | 21 ± 3* | 29 ± 2* | 11 ± 1* |
| Exodus COS cell supernatant (0.1 ml in 2 ml total medium) | 24 ± 4* | 27 ± 5* | 11 ± 2* |
| Exodus COS cell supernatant (0.05 ml in 2 ml total medium) | 23 ± 5* | 36 ± 3* | 14 ± 1* |
| Exodus COS cell supernatant (0.025 ml in 2 ml total medium) | 47 ± 8 | 58 ± 6 | 24 ± 1 |
| pECE-only COS cell supernatant (0.2 ml in 2 ml total medium) | 50 ± 6 | 60 ± 7 | 23 ± 3 |

*p < 0.005 (the other values are not significantly different from control or pECE at p < 0.05)

The Exodus in the COS cell supernatant inhibited hematopoietic progenitor colony formation in a dose-dependent manner, slightly more efficiently than a maximal dose of MIP-1α. There was no statistical difference between COS cell medium alone and medium from COS cells that had been tranfected with the empty pECE expression vector. At 50 ng/ml of recombinant human MIP-1α, a dose at which the biological effect plateaus, there was statistically significant reduction of both CFU-GM (43% of medium control), BFU-E (66% of control), and CFU-GEMM (50% of control). At the highest concentrations of recombinant Exodus used in these experiments there was also a statistically significant decrease in both CFU-GM (42% of control), BFU-E (48% of control), and CFU-GEMM (48% of control).

This inhibition by Exodus was dose-dependent, in that the three highest levels of Exodus showed inhibition of the proliferation of hematopoietic progenitors as measured by colony formation assays. However, the lowest concentration of Exodus used did not show such an inhibition. Like MIP-1α, Exodus inhibited progenitors in a multi-lineage fashion.

Purified synthetic Exodus was also tested in this assay. Results are shown in Table 2 below, which displays the mean count of hematopoietic progenitor colonies per plate, plus or minus the standard deviation.

TABLE 2

| Concentration of Chemokine in Medium | CFU-GM | BFU-E | CFU-GEMM |
|---|---|---|---|
| Control (no chemokine) | 85 ± 3 | 97 ± 4 | 39 ± 3 |
| Exodus (200 ng/ml) | 43 ± 11 | 43 ± 2 | 19 ± 3 |
| Exodus (100 ng/ml) | 39 ± 3 | 41 ± 2 | 20 ± 2 |
| Exodus (50 ng/ml) | 42 ± 10 | 42 ± 3 | 17 ± 2 |
| Exodus (25 ng/ml) | 41 ± 2 | 50 ± 2 | 20 ± 4 |
| Exodus (12.5 ng/ml) | 51 ± 3 | 70 ± 10 | 27 ± 1 |
| Exodus (6.25 ng/ml) | 64 ± 8 | 87 ± 3 | 32 ± 2 |
| MIP-1α (100 ng/ml) | 41 ± 2 | 44 ± 3 | 19 ± 2 |
| IL-8 (100 ng/ml) | 42 ± 2 | 44 ± 2 | 19 ± 2 |
| PF-4 (100 ng/ml) | 42 ± 4 | 44 ± 5 | 19 ± 1 |
| RANTES (100 ng/ml) | 81 ± 7 | 99 ± 4 | 37 ± 1 |
| NAP-2 (100 ng/ml) | 83 ± 2 | 93 ± 3 | 39 ± 4 |

There was a statistically significant (Student's T test) reduction in colony formation of all three types at concentrations of Exodus down to 25 ng/ml (p<0.005). The purified synthetic Exodus behaves identically to the Exodus in the COS cell supernatants. Both sources of Exodus are effective at inhibiting hematopoietic marrow progenitor proliferation, at least as good if not better than MIP-1α.

Similar results showing inhibition of the proliferation of hematopoietic progenitors, as measured by colony formation assays, were obtained with a purified synthetic Exodus protein product, which was Exodus with an additional alanine after residue 4.

These results show that Exodus protein products inhibited proliferation of hematopoietic progenitors. Indeed, Exodus protein products were as effective as MIP-1α. This indicates that Exodus protein products will be useful as cycle-specific chemoprotective agents.

Further experiments confirmed the effect of Exodus protein product in vivo on hematopoiesis in mice. Experiments were carried out essentially as described in Broxmeyer et al., *Ann. Hematol.*, 71:235–246 (1995), using untreated pure synthetic Exodus and Exodus treated with a 30% acetonitrile/1% trifluoroacetic acid (ACN) solution as described in Mantel et al., *Proc. Natl. Acad, Sci, USA*, 90:2232–2236 (1993). For chemokines which exist in solution as multimers, treatment with ACN stimulates formation of monomers, which are the active form in vivo, and thus enhances chemokine activity. ACN-treated chemokines can be active at concentrations 200-fold lower than untreated chemokines.

Figure 2:
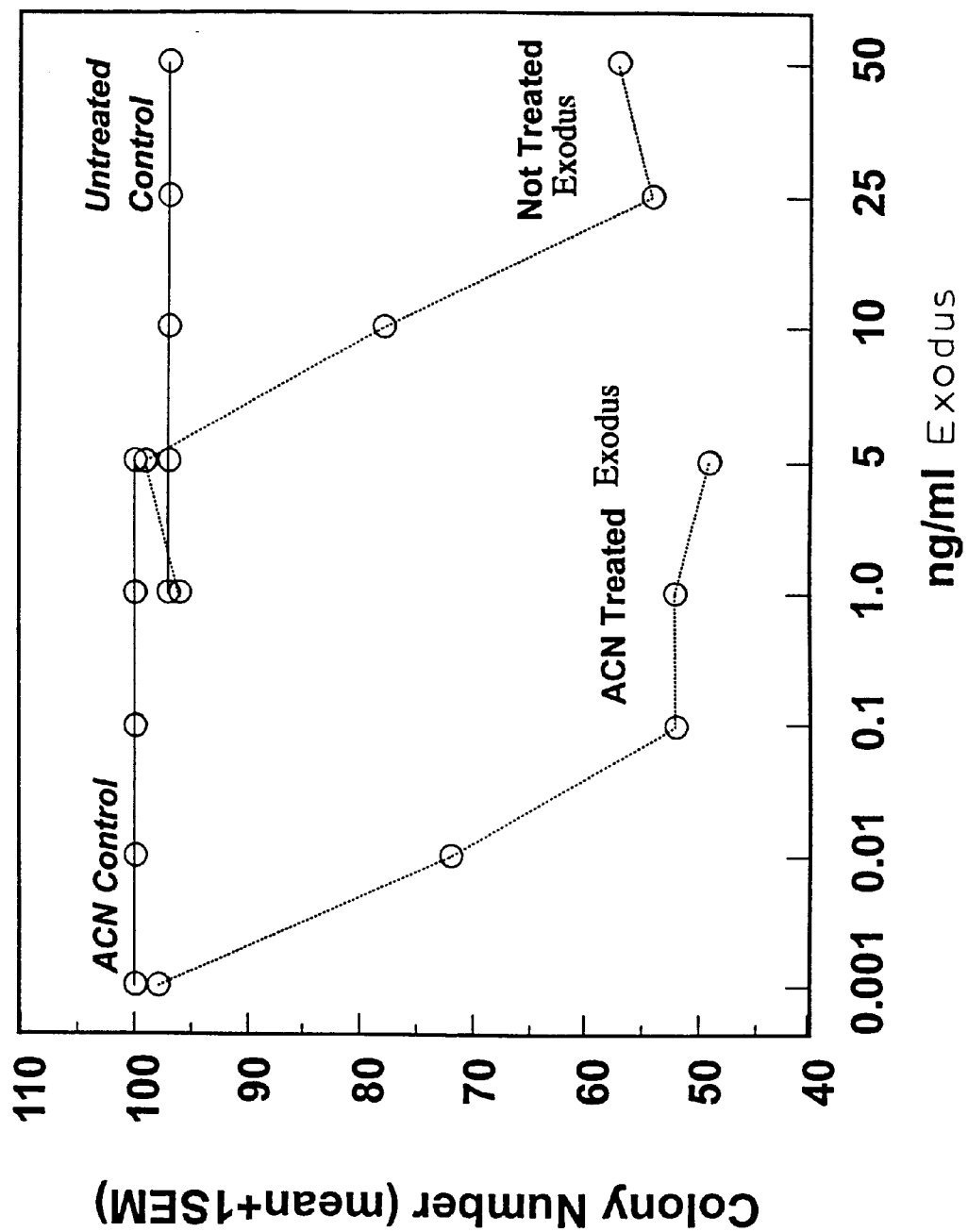
FIG. 2 shows the effect of untreated and ACN-treated Exodus on hematopoiesis in mice.

Briefly, solutions of untreated Exodus or ACN-treated Exodus were prepared at concentrations varying from 0.001 to 50 ng/ml Exodus. ACN-treated or untreated diluent served as a control to show that the ACN was not toxic. Normal C3H/HeJ mice were injected intravenously with a 0.2 ml dose of each solution and were sacrificed after 24 hours. Unseparated bone marrow cells were obtained from their femurs and were plated in either agar with 10% v/v pokeweed mitogen mouse spleen cell-conditioned medium (PWMSCM), for CFU-GM assessment, or in methylcellulose with human erythropoietin (Epogen®, Amgen, Thousand Oaks, Calif.), PWMSCM and hemin (Eastman Kodak Co., Rochester, N.Y.), for BFU-E/CFU-GEMM assessment. Colony counts were determined after seven days of incubation in a humidified environment in an ESPEC $N_2$—$O_2$—$CO_2$ incubator BNP-210 (Taboi ESPEC Corp., South Plainfield, N.J.) in 5% $CO_2$ and 5% $O_2$. Results are displayed in FIG. 2.

The results showed that untreated Exodus reduced CFU-GM colony formation to an average of 56% of control when a single dose of 0.2 ml of 25 ng/ml Exodus was injected. ACN-treated Exodus reduced CFU-GM colony formation to an average of 53% of control when a single dose of 0.2 ml of 0.1 ng/ml Exodus was injected. The inhibition of in vivo CFU-GM formation induced by both the ACN-treated and the untreated Exodus was statistically significant at p<0.05.

Figure 3:
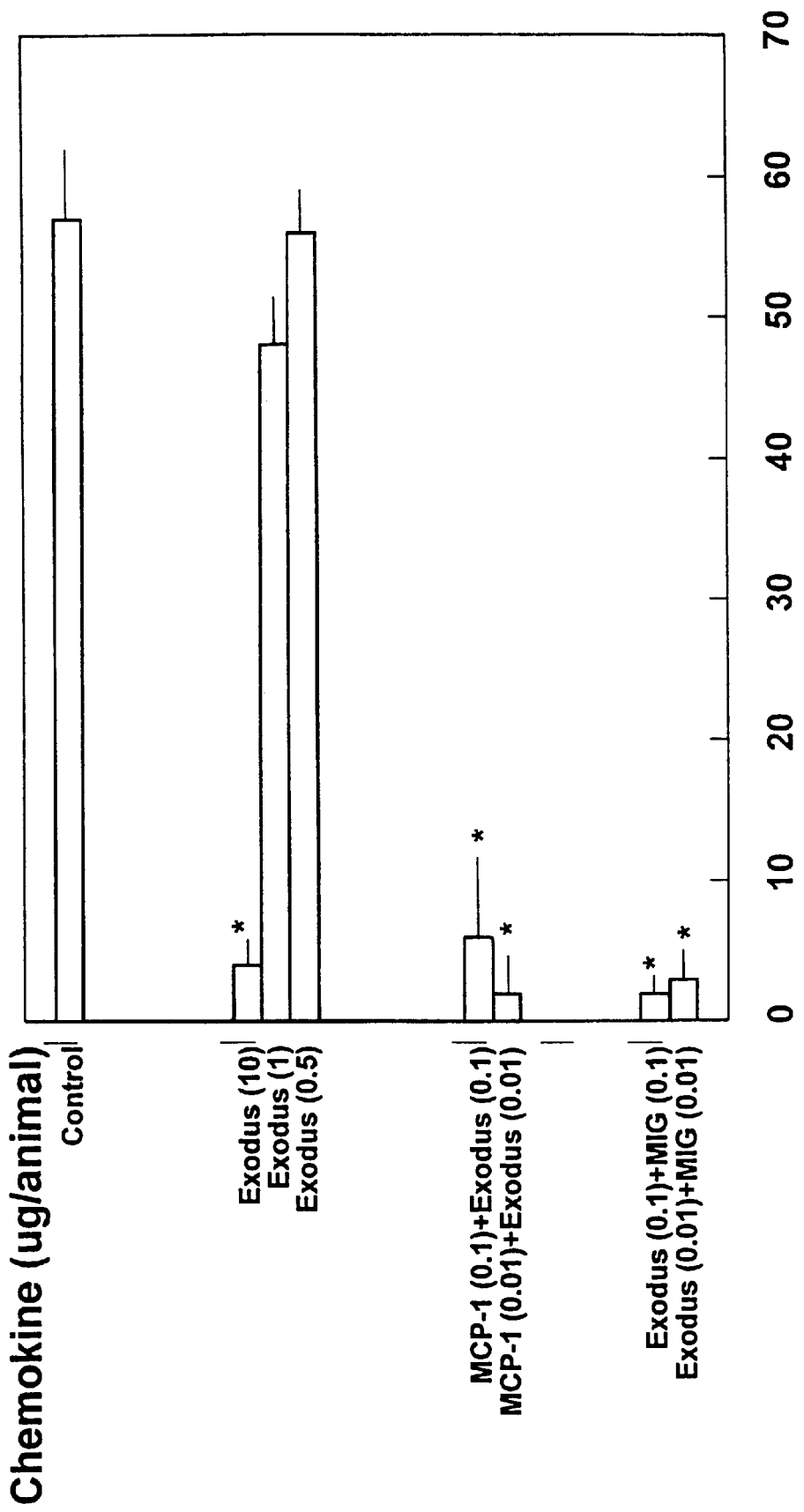
FIG. 3 shows the effect of Exodus alone or with MCP-1 or MIG on cell cycling of hematopoietic progenitors in mice.

In another experiment, the effect of untreated Exodus on the in vivo cycling of hematopoietic progenitors was evaluated with a tritiated thymidine kill assay essentially as described in Broxmeyer et al., Ann. Hematol., supra and in Mantel et al., Proc. Natl. Acad. Sci., supra. Briefly, mice were treated with varying concentrations of untreated Exodus (0.5, 1 or 10 ng/ml) alone or in combination with other untreated chemokines (Exodus at 0.01 or 0.1 ng/ml with either MCP-1 or MIG at 0.01 or 0.1 ng/ml). The animals were then sacrificed after 24 hours and bone marrow was collected for a tritiated thymidine kill assay. Because cells in the S-phase of the cell cycle preferentially incorporate thymidine, they are killed by the incorporation of tritiated thymidine whereas cells that are not in S-phase are unharmed. The number of cells in S-phase is estimated by calculating the number of cells killed, based on control colony numbers of cells that were not treated with tritiated thymidine. The values are reported as a percentage of progenitors in S-phase and are normalized for the total number of progenitors per femur. Results for CFU-GM are shown in FIG. 3.

The results showed that a single injection of 10 ng/mouse of Exodus significantly reduced the percentage of CFU-GM progenitors in S-phase of the cell cycle to an average of 4% (p<0.001), as compared to an average control value of 56% of CFU-GM in S-phase. In addition, Exodus-induced inhibition of cell cycle progression for CFU-GM was synergistic with MCP-1 and MIG treatment. When very low concentrations of Exodus was injected with MIG or MCP-1, there was an even greater reduction of CFU-GM in S-phase. Thus, a combination of chemokines may produce a more potent inhibition of hematopoiesis.

These results indicate that Exodus can temporarily arrest cell cycle progression of bone marrow progenitor cells, and thus can be used to protect normal bone marrow against S-phase cytotoxic chemotherapy.

B. Effect on Myeloid Cell Lines

The effect of Exodus protein products on the proliferation of cytokine dependent myeloid cell lines was also tested. The human myeloid cell lines TF-1 and MO7E [Avanzi et al., Brit. J. Haematol., 69:359 (1988)] require GM-CSF and SCF for maximal proliferation. The cytokine-dependent primitive acute myeloid leukemia cell lines TF-1 and MO7E (both gifts from Dr. Hal Broxmeyer, Indiana University, Ind.) were cultured in RPMI 1640 (Life Technologies, Gaithersburg, Md.) plus 10% FCS (Hyclone) and 100 U/ml penicillin and 100 μg/ml streptomycin (tissue culture antibiotics, Life Technologies, Gaithersburg, Md.). This media was supplemented with granulocyte-macrophage colony stimulating factor (GM-CSF, 100 U/ml, Immunex, Seattle, Wash.) and stem cell factor (SCF, 50 ng/ml, Amgen, Thousand Oaks, Calif.) for normal log phase growth.

Figure 4:
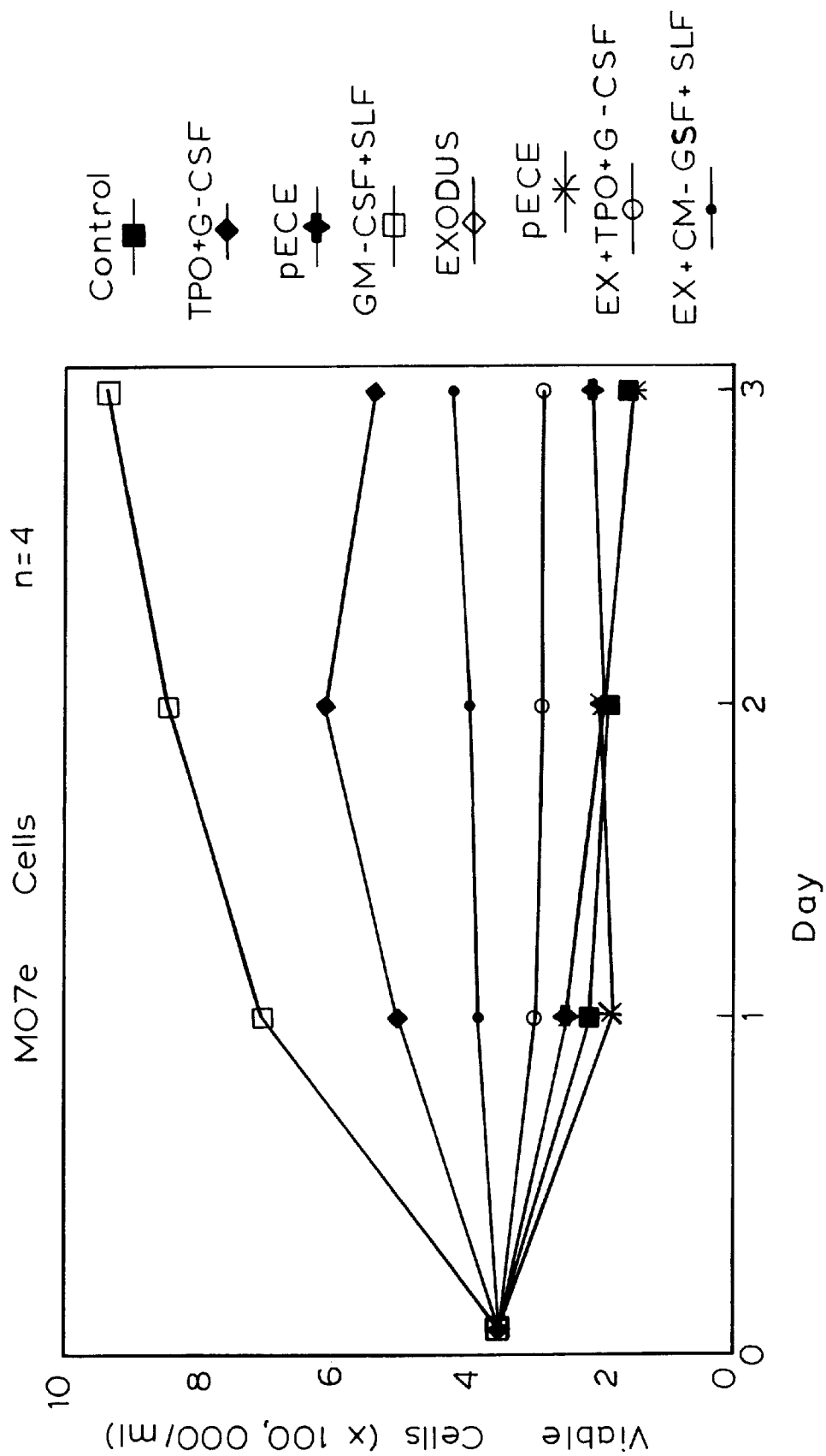
FIG. 4 shows the effect of Exodus on the proliferation of the myeloid cell line MO7E.
Figure 5:
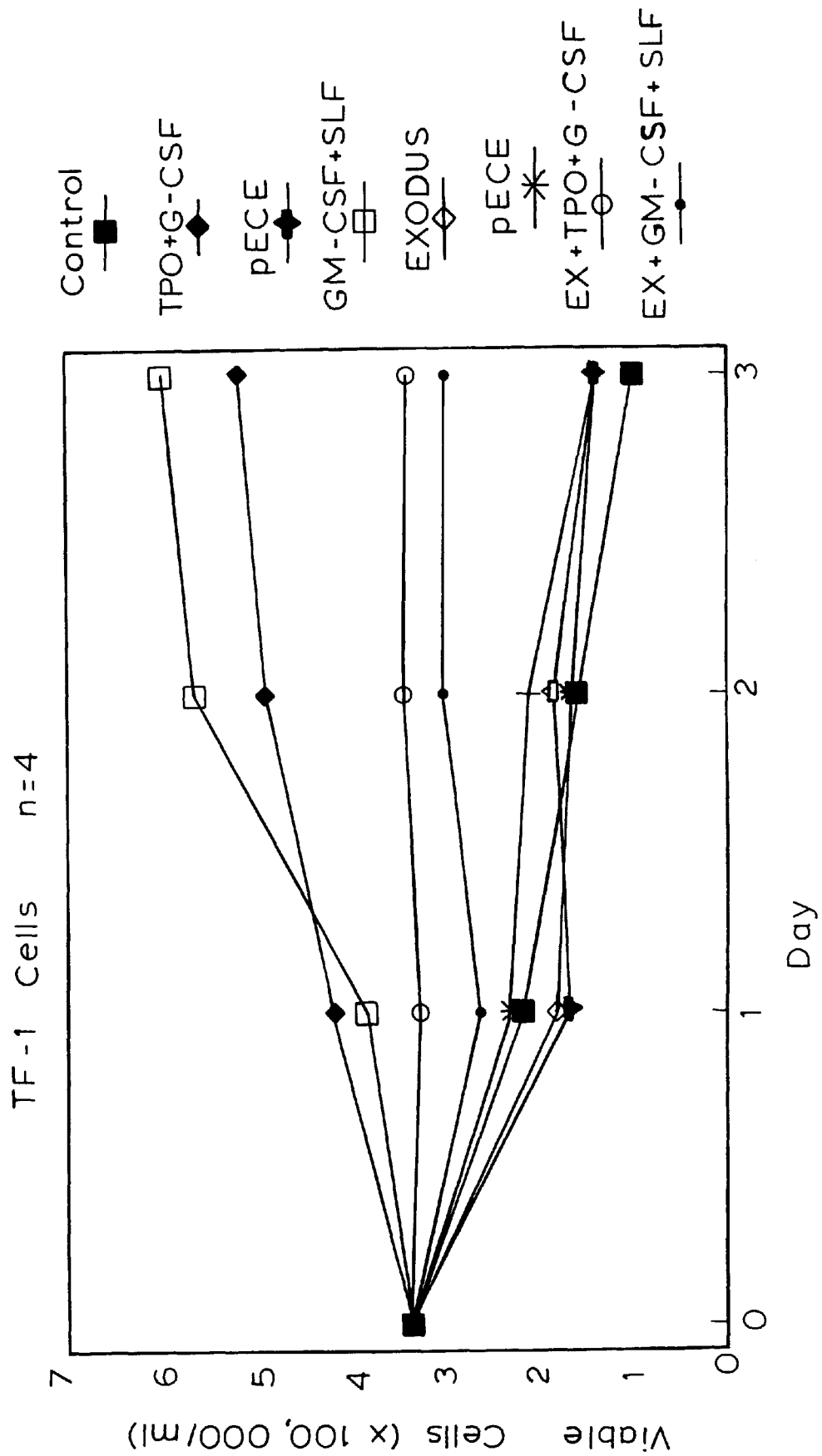
FIG. 5 shows the effect of Exodus on the proliferation of the myeloid cell line TF-1.

Exodus in COS cell supernatants prepared as described in Example 3 was tested at a final dilution of 1/10. Results are shown in FIG. 4 (for MO7E cells) and FIG. 5 (for TF-1 cells). When COS cell supernatant was added to log phase MO7E cells, in the presence of GM-CSF and SCF, proliferation over the next 72 hours was reduced to 10.4% of control. When COS cell supernatant was added to log phase TF-1 cells that were also continuously exposed to GM-CSF and SCF, proliferation was completely inhibited. Exodus was not exerting a cytotoxic effect, as the Exodus-treated cells had greater than 95% viability at every time point, as assessed by trypan blue exclusion, which was identical to that of the control cells.

Figure 6:
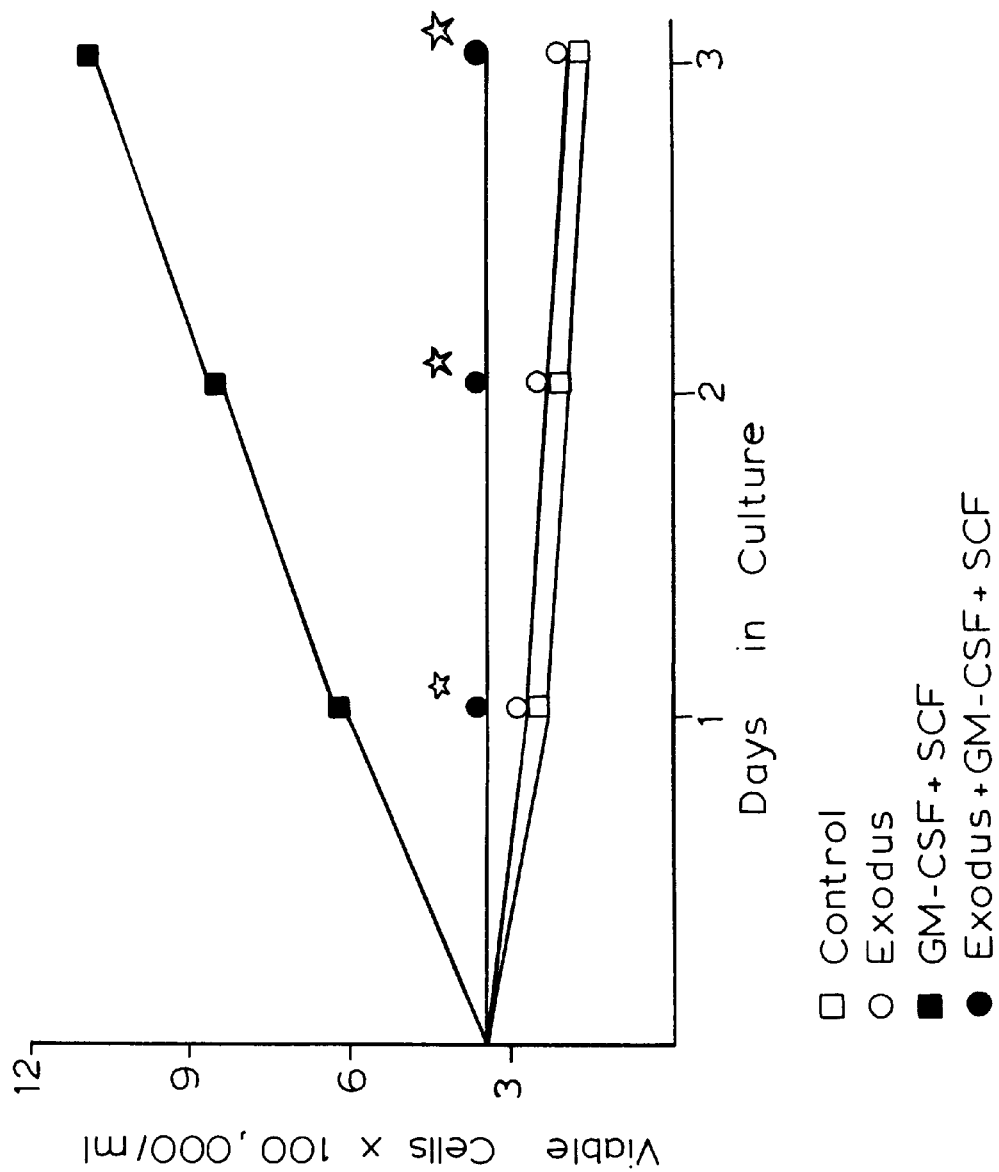
FIG. 6 shows the effect of purified synthetic Exodus on the proliferation of the myeloid cell line MO7E.

Purified synthetic Exodus also completely inhibited proliferation of the MO7E cells, as shown in FIG. 6. Each data point is the mean of four separate experiments. Stars denote statistical significance at p<0.05 using a paired t-test. Viability also did not change with the addition of Exodus.

These results indicate that Exodus will also be useful in treating myeloproliferative disorders such as chronic myelogenous leukemia.

C. Effect on Chronic Myelogenous Leukemia Progenitors

The effect of Exodus (also called "Exodus-1") on progenitor proliferation in chronic myelogenous leukemia (CML) was evaluated using colony formation assays as described in Hromas et al., Blood, 89:3315–3322 (1997). Briefly, bone marrow cells were collected from six CML patients in chronic phase. Low density marrow cells at $5 \times 10^4$ cells/mL were plated in 1% methylcellulose in Iscove's modified Dulbecco's medium supplemented with 30% fetal calf serum, 1 U/mL human erythropoietin (Epogen®, Amgen), 100 U/mL human interleukin-3 (Genetics Institute) and 50 ng/mL human stem cell factor (Amgen), in the presence or absence of 100 ng/ml Exodus and in the presence or absence of 100 ng/ml MIP-1α. Cultures were incubated at 5% $CO_2$ and low (5%) oxygen tension for 14 days, and then scored using an inverted microscope for CFU-GM, CFU-GEMM and BFU-E. Colony counts for cultures treated with Exodus or MIP-1α were compared to colony counts of the control cultures and were expressed as a percentage of control CFU or BFU. Data is displayed in Table 3 below.

TABLE 3

| Treatment | % of Control CFU-GM | % of Control BFU-E | % of Control CFU-GEMM |
| --- | --- | --- | --- |
| 100 ng/ml Exodus | 52 ± 5* | 44 ± 19* | 57 ± 6* |
| 100 ng/ml MIP-1α | 9 ± 3 | 1 ± 8 | 3 ± 6 |

*Statistically significant (p < 0.05) using unpaired Student's t-test.

These data demonstrate that in these six patients with CML in chronic phase, Exodus markedly inhibited progenitor colony formation. Exodus was much more effective than MIP-1α in suppressing proliferation, suggesting that the effects of Exodus are mediated by a receptor that MIP-1α does not activate.

CML progenitors overexpress the BCR-ABL fusion oncoprotein, a constitutively activated cytoplasmic tyrosine kinase that stimulates proliferation. In fact, forced overexpression of BCR-ABL in cell culture is transforming in many cell types, including NIH 3T3 cells. The effect of Exodus on the cell cycle progression of progenitors from three chronic phase CML patients was further explored using a tritiated thymidine kill assay as described above. Exodus treatment of the CML progenitors arrested cell cycle progression in an average of 55±5% of CFU-GM, 45±13% of BFU-E, and 50±10% of CFU-GEMM. Thus, the Exodus inhibitory signal was able to overcome the aggressive proliferative signal of BCR-ABL in CML progenitors.

These results indicate that Exodus suppresses hematopoiesis and may be effective for treating CML in chronic phase.

EXAMPLE 11

Effect of Exodus on HIV Proliferation

The ability of Exodus protein products to inhibit HIV proliferation, as measured by HIV production of p24 protein, was tested using a standard p24 ELISA assay as previously described in Cocchi et at., *Science*, 270:1811 (1996). Normal volunteer human peripheral blood mononuclear cells were isolated on a Ficoll gradient. These cells were activated with 1 ng/ml PHA (Sigma, St. Louis, Mo.) in RPMI 1640 (Life Technologies, Gaithersburg, Md.) plus 10% FCS (Hyclone) and 100 U/ml penicillin and 100 μg/ml streptomycin (tissue culture antibiotics, Life Technologies, Gaithersburg, Md.) for 48 hours at 37° C., washed in complete media, then infected with $TCID_{50}$=5000 of the HIV strains BAL (from ATCC) or A018-H112-2 (from ATCC) for 1 hour in complete media at 37° C. Cells were then washed three times in media to remove excess virus, and resuspended at $5 \times 10^5$ cells/0.3 ml per test in complete media plus recombinant human IL-2 (10 ng/ml, Boehringer-Mannheim, Indianapolis, Ind.) plus recombinant Exodus or pECE-transfected COS cell supernatants as controls. After six days of culture, cell-free supernatants were assessed for their content of HIV p24 using an enzyme-linked immunoabsorbent assay (ELISA, Abbott Laboratories, Chicago, Ill.). Experiments were performed in triplicate.

Figure 7:
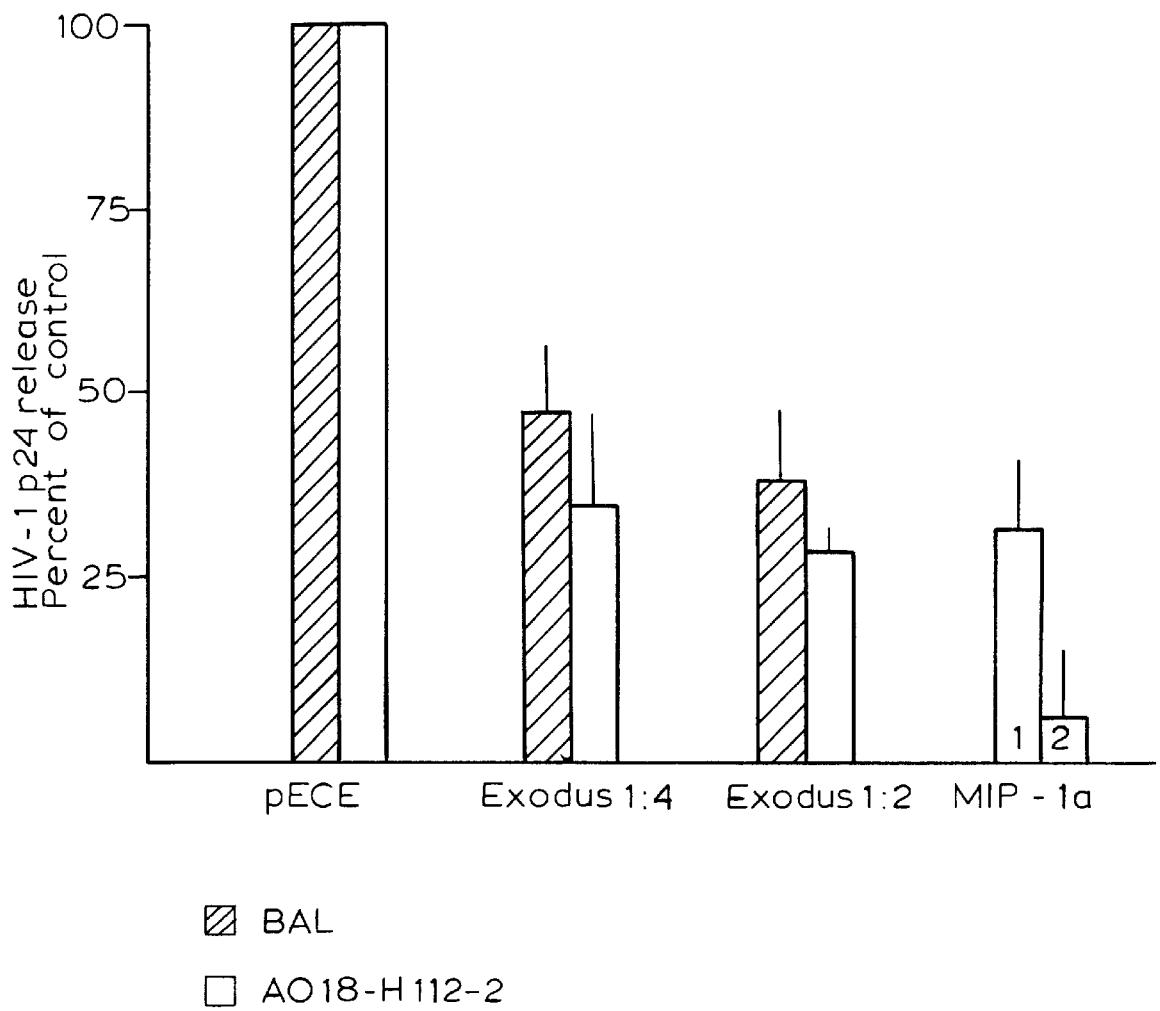
FIG. 7 shows the effect of Exodus on the release of HIV p24 protein by mononuclear cells after infection with HIV.

Exodus-containing COS cell supernatant at a final dilution of 1:2 (i.e., 0.15 ml of COS cell supernatant in 0.3 ml total in each well), Exodus-containing COS cell supernatant at a final dilution of 1:4, MIP-1α at 625 ng/ml and 1250 ng/ml (bar 1 and bar 2, respectively, in FIG. 7) and pECE COS cell supernatant (without Exodus) were measured at 6 days after infection. Results are shown in FIG. 7. When normal human peripheral blood mononuclear cells stimulated by PMA were infected at a high multiplicity with two strains of HIV, Exodus was able to significantly inhibit HIV proliferation in both strains. At the highest concentration of recombinant Exodus used, proliferation of the HIV strain BAL was decreased to 39% of control, while proliferation of the HIV strain A018 was reduced to 27% of control. This inhibition was less marked when the concentration of Exodus was reduced. In addition, this inhibition was consistent with that seen with MIP-1α, which was used as a positive control in these experiments. The inhibition by Exodus was not due to cytotoxicity, as there was no difference in the viability of cells treated with Exodus as with control cells.

Figure 8:
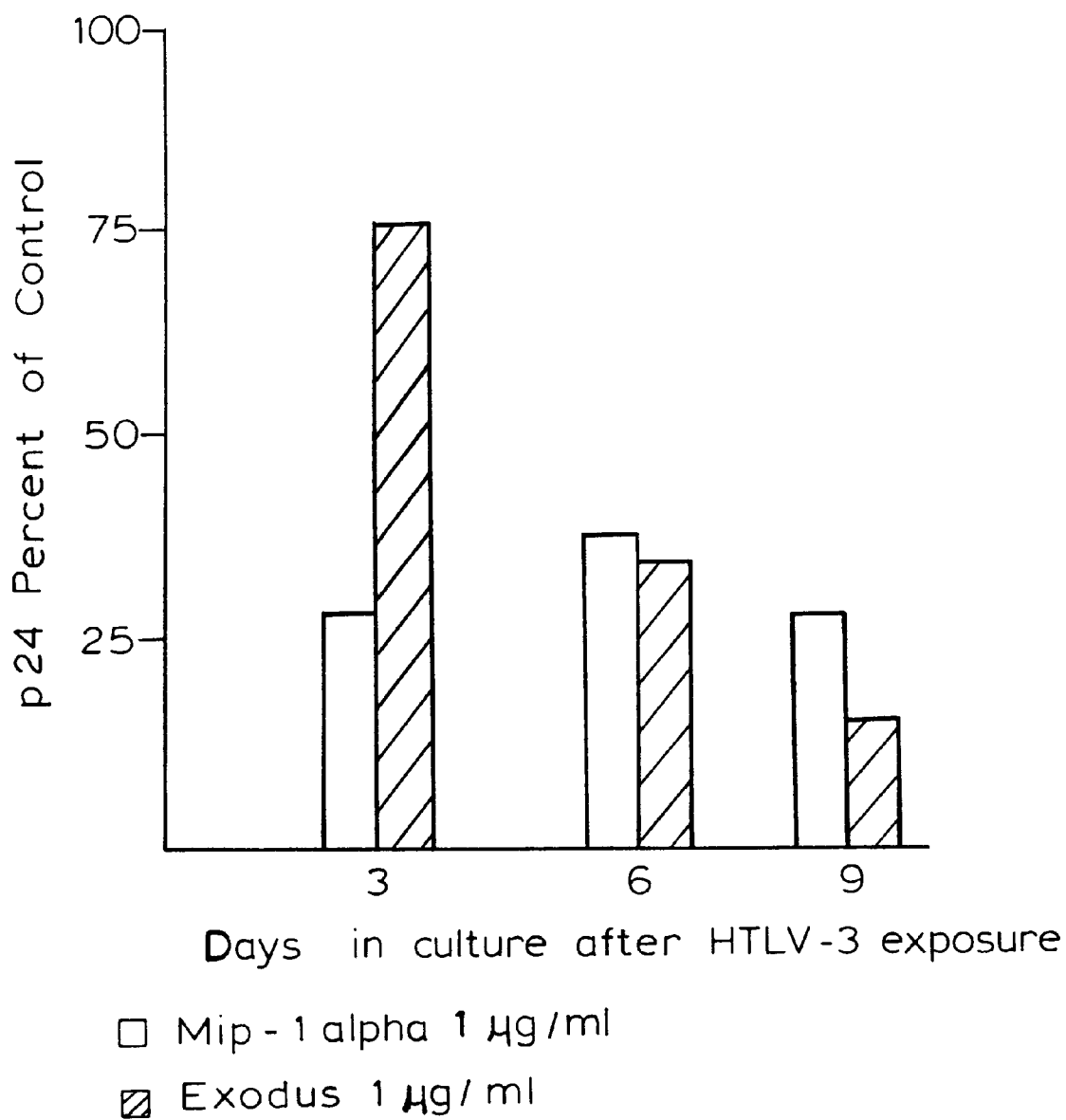
FIG. 8 shows the effect of purified synthetic Exodus protein product on the release of HIV p24 protein by mononuclear cells after infection with HIV.

Similar results for a purified synthetic Exodus protein product (Exodus with an additional alanine after residue 4) at a concentration of 1 μg/ml and MIP-1α at a concentration of 1 μg/ml are shown in FIG. 8. Results are shown at 3, 6, and 9 days after infection. At 9 days after infection, the inhibitory effect of Exodus was similar to that seen with MIP-1α at the same concentration. In this preliminary experiment, no effects were seen with this Exodus protein product at concentrations less than 1 μg/mL.

These results indicate that Exodus protein products inhibit the proliferation of HIV, and will therefore be useful in methods of increasing resistance to HIV infection and methods of treating HIV infection.

EXAMPLE 12

Assay of Chemoattractant and Cell-Activation Properties of Exodus on Human

Monocytes/Macrophages and Human Neutrophils

The effects of Exodus upon human monocytes/macrophages or human neutrophils is evaluated, e.g., by methods described by Devi et al., *J. Immunol.*, 153:5376–5383 (1995) for evaluating murine TCA3-induced activation of neutrophils and macrophages. Indices of activation measured in such studies include increased adhesion to fibrinogen due to integrin activation, chemotaxis, induction of reactive nitrogen intermediates, respiratory burst (superoxide and hydrogen peroxide production), and exocytosis of lysozyme and elastase in the presence of cytochalasin B. As discussed by Devi et al., these activities correlate to several stages of the leukocyte response to inflammation. This leukocyte response, reviewed by Springer, *Cell*, 76:301–314 (1994), involves adherence of leukocytes to endothelial cells of blood vessels, migration through the endothelial layer, chemotaxis toward a source of chemokines, and site-specific release of inflammatory mediators. The involvement of Exodus at any one of these stages provides an important target for clinical intervention by modulating the inflammatory response.

EXAMPLE 13

Exodus In Vivo Tumor Growth Inhibition Assay

Tumor growth-inhibition properties of Exodus are assayed, e.g., by modifying the protocol described by Laning et al., *J. Immunol.*, 153:4625–4635 (1994) for assaying the tumor growth-inhibitory properties of murine TCA3. An Exodus-encoding cDNA is transfected by electroporation into the myeloma-derived cell line J558 (American Type Culture Collection, Rockville, Md.). Transfectants are screened for Exodus production by standard techniques such as ELISA (enzyme-linked immunoadsorbant assay) using a monoclonal antibody generated against Exodus as detailed in Example 8. A bolus of 10 million cells from an Exodus-producing clone is injected subcutaneously into the lower right quadrant of BALB/c mice. For comparison, 10 million non-transfected cells are injected into control mice. The rate and frequency of tumor formation in the two groups is compared to determine efficacy of Exodus in inhibiting tumor growth. The nature of the cellular infiltrate subsequently associated with the tumor cells is identified by histologic means. In addition, recombinant Exodus (20 ng) is mixed with non-transfected J558 cells and injected (20 ng/day) into tumors derived from such cells, to assay the effect of Exodus administered exogenously to tumor cells.

EXAMPLE 14

Intraperitoneal Injection Assay

The cells which respond to Exodus in vivo are determined through injection of 1–100 ng of purified Exodus into the intraperitoneal cavity of mice, as described by Luo et al., *J. Immunol.*, 153:4616–4624 (1994). Following injection, leukocytes are isolated from peripheral blood and from the peritoneal cavity and identified by staining with the Diff Quick kit (Baxter, McGraw, Ill.). The profile of leukocytes is measured at various times to assess the kinetics of appearance of different cell types. In separate experiments, neutralizing antibodies directed against Exodus (Example 8) are injected along with Exodus to confirm that the infiltration of leukocytes is due to the activity of Exodus.

EXAMPLE 15

In vivo Activity Assay—Subcutaneous Injection

The chemoattractant properties of Exodus are assayed in vivo by adapting the protocol described by Meurer et al., *J. Exp. Med.*, 178:1913–1921 (1993). Recombinant Exodus (10–500 pmol/site) is injected intradermally into a suitable mammal, e.g., dogs or rabbits. At times of 4 to 24 hours, cell infiltration at the site of injection is assessed by histologic methods. The presence of Exodus is confirmed by immunocytochemistry using antibodies directed against Exodus. The nature of the cellular infiltrate is identified by staining with Baxter's Diff Quick kit.

EXAMPLE 16

Cloning of an Exodus Receptor

DNA encoding an Exodus receptor is cloned by adapting procedures previously described for isolation of the IL-8 receptor gene in Holmes et al., supra, and isolation of the MCP-1 receptor gene in Charo et al., supra.

A cDNA library is prepared, preferably from cells that respond to Exodus by cheinotaxis and activation. Radiolabelled Exodus can also be used to identify cell types which express high levels of receptor for Exodus. Cells which do not respond to MIP-1α or RANTES, or cells which show a different pattern of receptor desensitization in response to these ligands are of particular interest. Pools of transfected clones in the cDNA library are screened for binding of radiolabelled Exodus by autoradiography. Positive pools are successively subfractionated and rescreened until individual positive clones are obtained.

Alternatively, a degenerate PCR strategy may be used in which the sequences of the PCR primers are based on conserved regions of the sequences of known chemokine receptors. To increase the chance of isolating an Exodus receptor, the template DNA used in the reaction may be cDNA derived from a cell type responsive to Exodus.

While the present invention has been described in terms of specific embodiments, it is understood that variations and modifications will occur to those skilled in the art. Accordingly, only such limitations as appear in the appended claims should be placed on the invention.

---

What is claimed is:

1. A method of suppressing myeloproliferation comprising administering to a subject suffering from a myeloproliferative disease an amount of Exodus chemokine of SEQ ID NO: 2 or an analog thereof effective to suppress malignant bone marrow progenitor cell proliferation.

2. The method of claim 1 wherein the myeloproliferative disease is chronic myelogenous leukemia, essential thrombocytosis, myelofibrosis, or polycythemia vera.

* * * * *

UNITED STATES PATENT AND TRADEMARK OFFICE
CERTIFICATE OF CORRECTION

PATENT NO.    : 6,096,300
DATED         : August 1, 2000
INVENTOR(S)   : Robert Hromas It is certified that error appears in the above-identified patent and that said Letters Patent is hereby corrected as shown below:

Column 4,
Lines 9-10, replace "cheinokine" with -- chemokine --.

Column 5,
Lines 23-24, replace "phannaceutical" with -- pharmaceutical --.
Line 55, replace "tinder" with -- under --.

Column 11,
Line 20, replace "anti-tumor" with -- anti-tumor immunity. --.

Column 18,
Line 67, replace "Horik et al." with -- Horuk et al. --.

Column 23,
Line 4, replace "cheinotactic" with -- chemotactic --.
Line 31, replace "crythrocyte" with -- erythrocyte --.
Line 32, replace "CO" with -- $CO_2$ --.

Signed and Sealed this

Twenty-sixth Day of March, 2002

*Attest:*

*Attesting Officer*

JAMES E. ROGAN
*Director of the United States Patent and Trademark Office*